(12) United States Patent
Pan

(10) Patent No.: US 9,385,337 B2
(45) Date of Patent: Jul. 5, 2016

(54) NANOCRYSTALS ON FIBERS

(71) Applicant: Merck Patent GmbH, Darmstadt (DE)

(72) Inventor: Junyou Pan, Frankfurt Am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/373,661

(22) PCT Filed: Dec. 21, 2012

(86) PCT No.: PCT/EP2012/005359
§ 371 (c)(1),
(2) Date: Jul. 22, 2014

(87) PCT Pub. No.: WO2013/113349
PCT Pub. Date: Aug. 8, 2013

(65) Prior Publication Data
US 2015/0037203 A1 Feb. 5, 2015

(30) Foreign Application Priority Data
Jan. 30, 2012 (EP) .................................... 12000570

(51) Int. Cl.
*H01L 51/50* (2006.01)
*H01L 51/52* (2006.01)
*A61N 5/06* (2006.01)

(52) U.S. Cl.
CPC ............ *H01L 51/5032* (2013.01); *A61N 5/062* (2013.01); *A61N 5/0616* (2013.01); *A61N 5/0618* (2013.01); *A61N 5/0621* (2013.01); *A61N 5/0624* (2013.01); *H01L 51/502* (2013.01); *H01L 51/508* (2013.01);

(Continued)

(58) Field of Classification Search
CPC .................................................. H01L 51/5032
USPC ............................................................ 422/22
See application file for complete search history.

(56) References Cited

U.S. PATENT DOCUMENTS

| 6,538,375 B1 * | 3/2003 | Duggal et al. ................ 313/506 |
| 7,304,201 B2 * | 12/2007 | Holloway et al. ............... 602/41 |
| 9,093,656 B2 * | 7/2015 | Pan et al. |

(Continued)

FOREIGN PATENT DOCUMENTS

| WO | WO-2011076323 A1 | 6/2011 |
| WO | WO-2011110277 A1 | 9/2011 |

OTHER PUBLICATIONS

Cochrane et al., Flexible displays for smart clothing: Part I—Overview, Dec. 2011, Indian Journal of Fibre & Textile Research, vol. 36, p. 422-428.*

(Continued)

*Primary Examiner* — Kevin Joyner
*Assistant Examiner* — Holly Mull
(74) *Attorney, Agent, or Firm* — Drinker Biddle & Reath LLP

(57) ABSTRACT

The present invention relates inter alia to light- and/or irradiation-emitting fibers comprising nanocrystals, in particular quantum dots and nanorods, their preparation and use. The fiber may have a fiber core 10, an outer first electrode 20, a light emitting layer 30, a radiation transmissive second electrode 40 positioned over the organic light emitting layer 30. Eventually the fiber may also comprise an optional radiation transmissive moisture and/or air barrier layer 50 and/or an optional radiation transmissive encapsulating material 60.

21 Claims, 2 Drawing Sheets a)

b)

(52) U.S. Cl.
CPC ........ *H01L51/5064* (2013.01); *H01L 51/5287* (2013.01); *A61N 2005/0631* (2013.01)

(56) References Cited

U.S. PATENT DOCUMENTS

| | | | | |
|---|---|---|---|---|
| 2003/0099858 | A1* | 5/2003 | Duggal et al. | 428/690 |
| 2007/0198004 | A1* | 8/2007 | Altshuler et al. | 606/9 |
| 2007/0241662 | A1* | 10/2007 | Choi et al. | 313/502 |
| 2008/0286145 | A1* | 11/2008 | Ratcliffe | 422/24 |
| 2010/0123155 | A1* | 5/2010 | Pickett et al. | 257/98 |

OTHER PUBLICATIONS

International Search Report for PCT/EP2012/005359 mailed Feb. 1, 2013.

* cited by examiner a) b)

ns the the# NANOCRYSTALS ON FIBERS

CROSS-REFERENCE TO RELATED APPLICATIONS

This application is a national stage application (under 35 U.S.C. §371) of PCT/EP2012/005359, filed Dec. 21, 2012, which claims benefit of European Application No. 12000570.7, filed Jan. 30, 2012, both of which are incorporated herein by reference in their entirety.

The present invention relates inter alia to radiative fibers, their preparation and use in, e.g., lighting, display technologies, medical and cosmetic applications.

Thin film electroluminescent devices for organic light emitting diodes (OLEDs) and Quantum-dot light emitting diode (QD-LED), have drawn much attention since two decades, because they are, e.g., intrinsically flexible, and can be easily coated on large area by cheap methods, such as printing technologies like ink jet printing or screen printing. Therefore, such electroluminescent devices are very promising devices for large area applications like general lighting and display technologies. Actually, OLEDs can already be found in selected marketed products such as the display of cell phones or digital cameras.

Another filed of application for thin film electroluminescent devices is phototherapy. Phototherapy (also called light therapy) can be employed in a wide range of diseases and/or cosmetic (also called aesthetic) conditions. The therapy using light, either from LED or laser, is already being used to treat wounds, injuries, neck pain, osteoarthritis, the side effects of chemotherapy and radiotherapy, for instance.

Many diagnostic tools or devices also often require light sources, e.g., in order to determine blood characteristics such as bilirubin, oxygen, or CO. In both cosmetics and medicine the skin is the main target to be radiated, but other targets of the human or animal body can also be accessed by phototherapy. These targets include, but are not limited to, the eye, wounds, nails, and internal parts of the body. Light can also be used in order to facilitate or support disinfection of wounds, surfaces of more or less solid objects, liquids, and beverages, for example. More or less solid surfaces as used herein include any surface with plasticity or elasticity which is not a liquid. Many objects fall in this category and comprise, e.g., nutrition, cuterly, instruments for use in hospitals and surgery and any other object that requires a disinfection. Even wounds of humans and animals can also be subsumed under this definition.

One of the primary effects of phototherapy is the stimulation of metabolism in the mitochondria. Certain wavelengths of light stimulate cytochrome c oxidase, an enzyme which is responsible for the production of essential cellular energy in the form of adenosine triphosphate (ATP). ATP is required for cellular energy transfer in order to drive thermodynamically unfavoured biochemical reactions and as cellular energy storage. ATP can also act as signal molecule in order to modulate other biochemical molecules (e.g. reactive oxygen species and nitric oxide) that lead to ageing and cell death (oxidative stress). After phototherapy, the cells show an increased metabolism, they communicate better and they survive stressful conditions in a better way.

This principle can be used in many medicinal therapeutic and cosmetic applications, such as wound healing, connective tissue repair, tissue repair, prevention of tissue death, relief of inflammation, pain such pain in muscles or joints, acute injuries, chronic diseases, metabolic disorders, neurogenic pain and seasonal effect disorders.

Another area of the application of light is the treatment of various cancers. In cancer therapy photodynamic therapy (PDT) plays an important role. In PDT light may be used in conjunction with a pharmaceutical. These therapies can be used to treat a variety of skin and internal diseases. In PDT, a light-sensitive therapeutic agent known as a photopharmaceutical is supplied externally or internally to an area of the body which is to be treated. That area is then exposed to light of a suitable frequency and intensity to activate the photopharmaceutical. A variety of photopharmaceutical agents are currently available. For example there are topical agents such as 5-aminolevulinic acid hydrochloride (Crawford Pharmaceuticals), methylaminolevulinic acid (Metfix®, Photocure). There are also injectable drugs used primarily for internal malignancies, including Photofin® (from Axcan) and Foscan® (from Biolitech Ltd). Often, the drug is applied in a non-active form that is metabolised to a light-sensitive photopharmaceutical.

In photodynamic therapy, the primary technique for supplying light to the photopharmaceutical is to project light of a suitable wavelength from standalone light sources such as lasers or filtered arc lamps. These sources are cumbersome and expensive, and are therefore only suitable for use in hospitals. This leads to inconveniences for the patient, and high cost for the treatment. High light irradiances are needed in order to treat an acceptable number of patients per day (for the treatment to be cost effective) and to avoid unduly inconveniencing the patient.

So far, quite different devices have been developed for the above mentioned applications.

WO 98/46130 and U.S. Pat. No. 6,096,066 disclose arrays of LEDs for the use in photodynamic therapy. The small LED sources taught therein result in uneven light incident on the patient. Fabrication of arrays is complicated because of the large number of connections required. The devices shown therein are designed for hospital treatment.

GB 2360461 discloses a flexible garment which uses a conventional photodynamic therapy light source to produce light which is then transmitted through optical fibres. As such light sources are heavy, the device is not ambulatory and is limited to hospital use.

U.S. Pat. No. 5,698,866 discloses a light source using over-driven inorganic LEDs. A heat-sinking mechanism is required, and the device is suitable only for hospital treatment.

WO 93/21842 disclose light sources using inorganic LEDs. Although transportable, the device is not suitable for ambulatory use by a patient at home and clinical treatment is envisaged.

Beside LEDs, OLEDs have been proposed for the same purpose. In contrast to LEDs, OLEDs are intrinsically flexible, and can be coated on large area by, for example, printing technologies, such as ink jet printing and screen printing.

Rochester et al. disclosed in GB 24082092 a flexible medical light source such as an OLED comprising flexible light emitting diodes on a flexible substrate and resulting diagnostic devices directed to monitor blood characteristics (e.g. levels of CO, oxygen, or bilirubin) and phototherapeutic devices for the treatment of ailments.

Vogle Klaus and Kallert Heiko disclosed in EP 018180773 a device for the treatment of skin. The device comprises an potentially flexible organic light emitting diode (OLED) as light source. The device can be integrated in clothes or plaster.

Attili et al. (Br. J. Dermatol. 161(1), 170-173. 2009) published a clinical open pilot study of ambulatory photodynamic therapy (PDT) using a wearable low-irradiance OLEDs in the treatment of nonmelanoma skin cancer, suggesting that OLED-PDT is less painful than conventional PDT with the added advantage of being lightweight, and therefore has the potential for more convenient PDT at home.

Samuel et al. disclosed in EP 1444008B15 an ambulatory device for the use in a therapeutic and/or cosmetic treatment, the device comprises an OLEDs and poly(p-phenylene vinylene) (PPV) is used as an example.

EP 1444008 discloses devices comprising OLEDs for the treatment of photodynamic therapy.

WO 2011/069590 discloses a therapeutic device based on organic light emitting electrochemical cells (OLEC, LEC or LEEC). OLECs represent another type of organic electroluminescent device. They comprise ionic components responsible for charge transport in the device, as originally reported by Pei et al., in Science, 1995, 269, pp 1086. OLECs do not require Ba or Ca as cathode, are simple in their structure and can be manufactured easily.

Quantum-dot light (QD) emitting diodes (QD-LEDs) represent another technology based on nano-crystals, which were firstly reported by Alivisatos et al., "Light emitting diodes made from cadmium selenide nanocrystals and a semiconducting polymer", Nature (London) 370[6488], 354-357, 1994, where a multilayer consisting of QDs was sandwiched between PPV (poly(p-phenylene-vinylene)) and an electrode, giving emission in red upon applying voltage. Bulovic et al., "Electroluminescence from single monolayers of nanocrystals in molecular organic devices. Nature (London) 420[6917], 800-803, 2002 describe use of a single monolayer of CdSe QDs sandwiched between two organic layers.

Electroluminescent fiber devices have also been proposed. OLED fibers have been disclosed recently in U.S. Pat. No. 6,538,375 B1, US 2003/0099858, and by Brenndan O'Connor et al. (Adv. Mater. 2007, 19, 3897-3900). Single OLED fibers and their use in lighting is disclosed. However, the OLED fibers disclosed so far were aimed for display and general lighting applications.

Many applications in the fields of lighting, display, or medicine and cosmetics, require specific requirement regarding the light source, such as:
1) Narrow emission band for display application to achieve pure color and high efficiency;
2) Emission angle more than 180° C., for lighting and some medical applications;
3) Polarised light source for backlit in display, or even for 3D-display.
4) Flexible and portable devices, which is of particular importance for medical and cosmetic applications.

Electroluminescent devices developed so far can only partially meet these requirements. For example, LED has narrow emission, but is not flexible and cannot be made in large area; Fiber OLED or OLEC can given angle-independent light source, but with broad emission; Some polarised OLEDs have been reported, for example by stretch alignment (by Cimrova et al., Adv. Mater. 1996, 8, 146) or rubbing alignment of the emissive polymer (by Jandke at el., in Adv. Mater. 1999, 11, 1815), however mechanical modification of the polymer film is not desired for OLED performance, and their emission is intrinsically broad. QD-LED can be made flexible and on large area, but polarised emission from QD-LED isn't known to date, and the performance of QD-LED is still far from OLED. A few polarised LEDs based on nanorods are reported, for example Rizzo et al., reported in ACS Nano, 2009, 3, 1506. The authors, however, use a special self assembly and transfer technique, and the performance of the device is very low. There is, therefore, a strong need for the development of novel thin light sources which fulfil the above mentioned requirements, i.e. 1)+2)+4), or 1)+3)+4), or even 1)+2)+3)+4).

Surprisingly, electroluminescent fiber devices comprising nanocrystals, preferably quantum dots (QDs) and nanorods (NRs), solve the problems discussed above. It has been found by the inventors that using QDs in organic electroluminescent fiber devices such as OLEDs or OLECs new devices with specific light emission (wavelength and/or intensity) with high efficiency can be prepared. Furthermore the devices according to the present invention can be prepared in order to emit polarized light.

Nanocrystals, especially QDs and NRs, offer new ways to tailor fiber devices required for specific applications, in particular if flexibility of a device, and/or narrow emission, and/or polarised light are advantageous.

The present invention relates to an electroluminescent fiber (EL-F) comprising at least one emissive layer (EML) and at least one nanocrystal. The nanocrystal can be electrically neutral or ionic in nature. Preferably the electroluminescent fiber is an QD or NR light emitting device. The nanocrystal is preferably located in the EML.

Preference is given to said fiber device comprising one EML and at least one kind of nanocrystal, preferably 3, particularly preferably 2 and very particularly preferably 1 kind of nanocrystal.

The term fiber means a shape having a length which is much greater than the cross sectional diameter (or width or height for non-circular cross sections). In a preferred embodiment of the present invention, the term fiber means a shape that has rather large length to diameter ratio, such as 10:1 or greater. Particularly preferably, the length to diameter ratio is 100:1 or greater.

The EL-F according to the present invention comprise at least two electrodes. Preferably the said EL-F comprises exactly two electrodes, a first and a second electrode. In particular the EL-F comprises, in sequence:
a) a first electrode,
b) light emitting layer, and
c) a second electrode.

Further details on materials and device architecture are provided below.

The present invention also relates to said EL-F comprising a fiber core 10 (see FIG. 1). The fiber core may comprise a flexible or rigid, preferably flexible, fiber core 10 and the first electrode 20 over the outer surface of the fiber core member 10. Preferably, the fiber core member 10 has the non-planar outer surface, such as a circular outer surface, and the first electrode 20 is formed around the entire outer surface of the fiber core member 10, such that the electrode 20 also has a non-planar outer surface, such as a circular surface. In an alternative preferred aspect of the present invention, the fiber core member 10 may be omitted, and the fiber core may consist entirely of the first electrode 20, such as a metal electrode having an elongated fiber shape. The electrode 20 may be hollow or solid. Preferably, the electrode contains a non-planar outer surface, such as a circular surface.

The fiber core can be flexible or rigid and flexible fibers can either be ductile, i.e. it can be deformed plastically without fracture, or elastic, i.e. the fiber deforms reversibly and once the forces responsible for deformation are no longer applied, the object returns to its original shape. Preferably the fiber is flexible. By choosing the appropriate materials the degree of flexibility of the light emitting fibers can be tailored to any desired value.

The fiber core 10 may be transparent, translucent, opaque or reflective. The materials used can be glass, plastic, ceramic or metal foils, where plastic and metal foils are preferably used for flexible substrates. The fiber core member 10 may comprise a flexible polymeric or metallic material.

Suitable polymeric materials for fiber core member 10 are polyolefins such as polyethylene, polypropylene, or polytetrafluoroethylene; polysiloxane; epoxy, polyacrylate; polyethyleneterephtalate; and derivatives thereof. Fiber core element 10 may comprise a glass or a metal such as aluminium, copper, or steel.

The glass used can be, for example, soda-lime glass, Ba- or Sr-containing glass, lead glass, aluminium silicate glass, borosilicate glass, Ba borosilicate glass or quartz.

Plastic plates can consist, for example, of polycarbonate resin, acrylic resin, vinyl chloride resin, polyethylene terephthalate resin, polyimide resin, polyester resin, epoxy resin, phenolic resin, silicone resin, fluorine resin, polyether sulfide resin or polysulfone resin.

For transparent fiber cores, use is made, for example, of polyethylene, ethylene-vinyl acetate copolymers, ethylene-vinyl alcohol copolymers, polypropylene, polystyrene, polymethyl methacrylate, PVC, polyvinyl alcohol, polyvinylbutyral, nylon, polyether ether ketone, polysulfone, polyether sulfone, tetrafluoroethylene-perfluoroalkyl vinyl ether copolymers, polyvinyl fluoride, tetrafluoroethylene-ethylene copolymers, tetra-fluoroethylene-hexafluoropropylene copolymers, polychlorotrifluoro-ethylene, polyvinylidene fluoride, polyester, polycarbonate, polyurethanes, polyimide or polyether imide.

Other materials than those mentioned here can also be used as fiber core 10. Suitable materials are known to the person skilled in the art.

The core member preferably has a diameter (or height or width for non-circular cross sections) of about 1 μm to about 10 mm, particularly preferably 5 μm to 5 mm, and very particularly preferably 10 μm to 1 mm. The EL-F may further comprise a power source electrically connected to the cathode 20 and the anode 40. The power source may be a voltage source, such as a small battery, a printed battery or a plug that plugs into a socket. The power source is connected to the cathode 20 and the anode 40. The power source may also contain a switch which allows the user to turn the device on and off, and/or a brightness control, such as a potentiometer.

The device may comprise an interactive steering unit. The steering unit may, e.g., allow a switch from continuous illumination to pulsed illumination. It also may allow the precise adaptation of irradiation intensities and/or wavelengths to be emitted. The steering unit may be directly associated to the device. It can also be separated via a permanent or temporary linkage. The device may be disposable and is suitable for uses in the hospital or outside the hospital.

The steering unit may be used interactively by the user, patient, physician, nurse, or other persons. The steering unit can also be operated according to the specification of expert, e.g. a physician, by programming it.

While the EL-F as depicted in FIG. 1 has a circular cross section, it may have any other desired cross section. For example, the fiber may have an oval cross section, a polygonal cross section (e.g. a square cross section) or a combination of circular, oval or polygonal cross sections.

The light emitting fiber preferably has a diameter (or height/width for non-circular cross sections) of about 1 μm to about 2 mm, particularly preferably 5 μm to 1 mm, and very particularly preferably 10 μm to 0.5 mm.

The fiber can also comprises a metal contact element in contact with a first portion of the outer surface of the radiation transmissive anode 40. The purpose of the contact element is to reduce the voltage drop along the length of the EL-F, since a radiation transmissive anode material, such as indium tin oxide (ITO), may not have a high enough electrical conductivity to obtain the desired value of the voltage drop. The contact element may comprise any conductive metal, such as aluminum or copper. The moisture barrier layer 50 may comprise any material that prevents moisture from permeating into the organic layer 30, such as $SiO_2$, $Si_3N_4$ or silicon oxynitride. The encapsulation material 60 may comprise silicone or epoxy.

In one preferred embodiment the EL-F according to the present invention comprises:
a) a fiber core 10 (see FIG. 1) having an outer first electrode 20;
b) a light emitting layer (EML) 30 comprising at least one nanocrystal and/or at least one organic emissive compound and/or at least one ionic species, positioned over the outer surface of the said first electrode 20;
c) a radiation transmissive second electrode 40 positioned over the organic light emitting layer 30.

FIG. 1 schematically depicts the setup of an EL-F (FIG. 1a and cross sectional view in FIG. 1 *b*). Preferably the first electrode 20 is a cathode and the second electrode 40 is an anode. On the outer surface of the anode may be a metal contact element having a first surface in contact with a first portion of an outer surface of the anode, and a power source electrically connected to the cathode and the metal contact element.

As already mentioned, the first electrode 20 may be a cathode and the second electrode 40 may be a light transmissive anode. However, the polarity of the electrodes 20, 40 may be reversed, and electrode 20 may be the anode and electrode 40 may be the cathode.

If desired, the EL-F may also comprise an optional radiation transmissive moisture and/or air barrier layer 50 and/or an optional radiation transmissive encapsulating material 60, as illustrated in FIG. 1. The inner surface of layer 50 surrounds the outer surface of the anode 40, and the inner surface of material 60 surrounds the outer surface of the layer 50, if layer 50 is present, or the outer surface of the anode 40.

If desired, the EL-F may also comprise an optional refractive index matching layer. The inner surface of the refractive index matching layer surrounds the outer surface of the anode 40, and the inner surface of material 50 surrounds the outer surface of refractive index matching layer, if layer 50 is present. Such refractive index matching layers are helpful for light out-coupling. Suitable materials are dielectric materials with a high refractive index such as CsCl, NPB, C60, MeO-TPD, ZnO, 2,9-dimethyl-4,7-diphenyl-1,10-phenanthroline (BCP), $Alq_3$, Au, and $SnO_2$. The thickness of the index matching layer can be in the range between 1 and 300 nm, preferably in the range between 5 and 100 nm, and particularly preferably in the range between 10 and 60 nm. More details on refractive index matching can be found in US 20080231959 A1.

The light emitting fiber has a high brightness and can be made flexible if it has a fiber or tube shape. The fiber or tube shaped EL-F may have an improved moisture resistance while remaining flexible, in contrast to prior art flat plate OLEDs, by adding an outer moisture/air barrier layer and/or by forming an outer moisture and air impervious metal electrode around the fiber core.

The EL-F according to the present invention can emit one ore more wavelengths or ranges of wavelengths. Different wavelengths (or ranges of wavelengths) can be achieved by the use of more than one light emitting layer 30 in one fiber with different nanocrystals and/or organic emissive materials emitting light of different wavelengths or ranges of wavelengths. Preferably the light emitting fiber according to the present invention comprises 3, particularly preferably 2, and very particularly preferably 1 light emitting layer 30.

The light emitting layer 30 can also comprise different emissive materials in one light emitting layer. Preferably the radiation emitting layer 30 comprises 3, particularly preferably 2, and very particularly preferably 1 emissive materials. The different emissive materials are selected from the nanocrystal or organic emissive materials as described below, but any other emissive material suitable can be employed. If two emissive materials are used in one emissive layer the absorption spectrum of one of the two emissive materials preferably overlaps with the emission spectrum of the other emissive material.

Different wavelengths can also be accomplished by dividing the light emitting fiber into small segments having n distinct light emitting layer 30 as depicted in FIG. 2a) and b) emitting n different wavelengths or ranges of wavelengths. If multiple segments are used in one fiber then n is preferably 4, particularly preferably 3, and very particularly preferably 2 (see FIG. 2b). Preference is also given to a n EL-F comprising multiple segments with n equals 1, i.e. each segment emits the same wavelength or ranges of wavelengths.

Devices emitting different wavelengths or ranges of wavelengths can also be obtained by employing different light emitting fibers as depicted in FIG. 3 and FIG. 4, whereby n is defined as above. Particular preference is given to a device comprising two distinct light emitting fibers (see FIG. 4).

The parallel arrangement of light emitting fibers in an device is only one possibility. Any processing known for fibers can be employed. The fibers can, e.g. be woven as depicted in FIG. 5. Hereby different light emitting fibers can be processed in order to get a canvas emitting different wavelengths or ranges of wavelengths. The fibers emitting the same wavelength(s) can be arranged in parallel to each other so that fibers emitting different wavelength(s) are peripendicular to each other (FIG. 6). The fibers emitting different wavelength(s) can also be arranged in an alternating fashion.

The radiation emitting layer 30 has a thickness in the range between 440 nm and 0.5 mm, preferably in the range between 100 nm and 0.1 mm, particularly preferably in the range between 200 nm and 50 µm, and very particularly preferably in the range between 500 nm and 10 µm and the electrodes 20, 40 each have a thickness in the range between 10 and 1000 nm, preferably in the range between 20 and 200 nm, and particularly preferably in the range between 20 and 100 nm.

The radiation emitting fiber may also include an optional radiation scattering layer, comprising scattering particles such as $TiO_2$, $Al_2O_3$, or $SiO_2$ for effective color mixing and brightness uniformity. The scattering particles can also be mixed into the encapsulating material 60, or be formed as a separate layer over the encapsulating material 60, if desired. A variety of radiation emitting layers 30 can be used in conjunction with exemplary embodiments of the invention.

Suitable materials for both anode and cathode are all metaly and their alloys, preferably selected form Al, Ag, Au, Pt, Cu, Fe, Ir, Mo, Pd, Sn, V, Co, Ni, W, Ga, Ta, Sb, Zn, In, mixtures of two or more elements such as alloys comprising Mg/Al or Al/Li or Mg/Ag, metal oxides preferably selected from, but not limited to, indium tin oxide (ITO), indium zinc oxide (IZO), tin oxide (SnO), ZnO, InO, aluminium-zinc-oxide (AlZnO), and other metal oxides such as Al- and In-zinc oxide doped with zinc oxide, magnesium-indium-oxide, and nickel-tungsten-oxide. Metal nitrides such as galliumnitrides and metal selenides such as zinc-selenide and metal-sulfides such as zinc-sulfide can also be used. Further materials that can be used for electrodes (i.e. anodes and cathodes) are electrically conducting polymers, e.g. polythiophenes, polyanilines and polypyrroles or other conductive polymers, such as disclosed by M. S. Freud and B. A. Deore in "Self-Doped Conducting Polymers", John Wiley & Sons, Ltd, 2007.

The electrodes, i.e. anode and cathode, can be independently from each other be transparent, opaque, or reflective. The anode can also adopt an intermediate state, e.g. both being partially reflective and partially transparent.

If the electrodes are not or only partially transparent further conducting materials can be used. Preferred materials for non transparent or partially transparent anodes are selected from, but not limited to, Au, Ir, Mo, Pd, Pt, Cu, Ag, Sn, C, Al, V, Fe, Co, Ni, W, and mixtures thereof. The conducting materials can also be mixed with further conducting materials as described above, e.g. In—Cu.

The anode is preferably transparent and a particularly preferred material for the anode is ITO. Further materials can be used for anodes, which are known to the person skilled in the art.

Further suitable materials for cathodes, used to form a thin dielectric layer, are selected from a metal which is mixed with LiF, $Li_2O$, $BaF_2$, MgO, or NaF. A typical combination is LiF/Al.

An Mg/Al cathode with ITO layer on top is described in U.S. Pat. No. 5,703,436, U.S. Pat. No. 5,707,745, U.S. Pat. No. 6,548,956 B2, U.S. Pat. No. 6,576,134 B2. An Mg/Ag alloy is described in U.S. Pat. No. 4,885,221.

The EL-F according to the present invention can comprise different organic functional materials, which include hole injection materials (HIM), hole transport materials (HTM), hole blocking materials (HBM), electron injection materials (EIM), electron transport materials (ETM), electron blocking materials (EBM), exciton blocking materials (ExBM), fluorescent emitters, phosphorescent emitters, host materials. In principle any known organic functional materials known to be used in organic light emitting cells can be used.

The materials may be selected from the group of small molecules, polymers, oligomers, or dendrimers, blends or mixtures thereof.

The term small molecule as used herein is defined as molecule not being a polymer, oligomer, dendrimer, or a blend. In particular, repeating structures are absent in small molecules. The molecular weight of small molecules is typically in the range of polymers with a low number of repeating units, oligomers or less.

The molecular weight of the small molecule is preferably below 4000 g/mol, particularly preferably below 3000 g/mol, and very particularly preferably below 2000 g/mol.

The polymers of the present invention preferably have 10 to 10000, particularly preferably 20 to 5000 and very particularly preferably 50 to 2000 repeat units. Oligomers according to this invention have preferably 2 to 9 repeat units. The branching index of the polymers and oligomers is between 0 (linear polymer without branching) and 1 (completely branched dendrimer). The term dendrimer as used herein is defined according to M. Fischer et al. in Angew. Chem., Int. Ed. 1999, 38, 885).

The molecular weight (MW) of the polymers of the present invention is preferably in the range of 10000 to 2000000 g/mol, particularly preferably in the range of 100000 to 1500000 g/mol, and very particularly preferably in the range of 200000 to 1000000 g/mol. The determination of MW can be performed according to standard techniques known to the person skilled in the art by employing gel permeation chromatography (GPC) with polystyrene as internal standard, for instance.

A blend is a mixture comprising at least one polymeric dendrimeric, or oligomeric component.

The fiber according to the present invention may also comprise at least one electrically neutral or ionic organic emissive compound preferably selected from fluorescent emitter materials, phosphorescent emitter materials, and emissive organo metallic complexes.

The EL-F comprises 4, preferably 3, particularly preferably 2, and very particularly preferably 1 organic emissive compound.

Preferably the EL-F comprises the organic emissive compound in a concentration range between 1 wt % and 30 wt %, particularly preferably between 2 wt % and 20 wt %, and very particularly preferably between 5 wt % and 15 wt % with respect to the total mass of the emissive layer.

In a preferred embodiment the EL-F comprises at least one host material and at least one emitter material, wherein the host material is selected from anthracenes, benzanthracenes, ketones, carbazoles, triarylamines, indenofluorenes, fluorenes, spirobifluorenes, phenanthrenes, dihydro-phenanthrenes, thiophenes, triazines, imidazoles, isomers and derivatives thereof, and the emitter can be nanocrystal or organic emitter.

Host materials are usually used in combination with emitter and have, in general, larger energy gaps between the HOMO and the LUMO as compared to emitter materials. In addition, host materials behave either as electron or hole transport material. Host materials can also have both electron and hole transport properties. In some embodiments, a maximal overlap between the absorption spectrum of the emitter with the photoluminescence spectrum of the host material is desired. This ensures the energy transfer from the host material to the emitter.

The term emitter refers to a material which, upon receiving excitonic energy by any kind of energy transfers from other materials, or by forming an exciton either electrically or optically, undergoes radiative decay to emit light. There are basically two classes of emitters, fluorescent and phosphorescent emitters. The term fluorescent emitter relates to materials or compounds which undergo a radiative transition from an excited singlet state to its ground state. The term phosphorescent emitter, as used herein, relates to luminescent materials or compounds which comprise transition metals. This typically includes materials emitting light caused by spin forbidden transition(s), e.g., transitions from excited triplet or quintet states.

The term dopant as employed herein is also used for the term emitter or emitter material.

Host material is also called matrix or matrix material, particularly if a host is meant which is used in combination with a phosphorescent emitter. In the case of a copolymer comprising emitter units, the polymer backbone acts as a host.

The EL-F comprises 4, preferably 3, particularly preferably 2, and very particularly preferably 1 host material.

Thus, the said EL-F may also comprise more than one host material. If the EL-F comprises more than one host material the host materials are also referred to as co-host or co-host materials.

In a very preferred embodiment, EL-F comprises in the emissive layer one nanocrystal, one organic fluorescent emitter and one host material. The suitable fluorescent emitters and host materials for such combination is described below.

Preferred blue fluorescent emitters to be employed in an EL-F according to the present invention are selected from polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-(bis(9-ethyl-3-carbazovinylene)-1,1'-biphenyl, fluorene, arylpyrenes (US 2006/0222886), arylenevinylenes (U.S. Pat. No. 5,121,029, U.S. Pat. No. 5,130,603), derivatives of rubrene, coumarine, rhodamine, quinacridone, such as, for example, N,N'-dimethylquinacridone (DMQA), dicyanomethylenepyrane, such as, for example, 4 (dicyanoethylene)-6-(4-dimethylaminostyryl-2-methyl)-4H-pyrane (DCM), thiopyrans, polymethine, pyrylium and thiapyrylium salts, periflanthene, indenoperylene, bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997), 1-48 and "Recent progress of molecular organic electroluminescent materials and devices" Mat. Sci. and Eng. R, 39 (2002), 143-222.

Preferred fluorescent dopants according to the present invention are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. The corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracene-amines, aromatic anthracene-diamines, aromatic pyrene-amines, aromatic pyrene-diamines, aromatic chrysene-amines and aromatic chrysene-diamines. An aromatic anthracene-amine is taken to mean a compound in which one diarylamino group is bonded directly to an anthracene group, preferably in the 9 position. An aromatic anthracene-diamine is taken to mean a compound in which two diarylamino groups are bonded directly to an anthracene group, preferably in the 9,10-position. Aromatic pyrene-amines, pyrene-diamines, chrysene-amines and chrysene-diamines are defined analogously thereto, where the diarylamino groups on the pyrene are preferably bonded in the 1 position or in the 1,6-position.

Further preferred fluorescent dopants are selected from indenofluorene-amines and indenofluorene-diamines, for example in accordance with WO 2006/122630, benzoindenofluorene-amines and benzoindenofluorene-diamines, for example in accordance with WO 2008/006449, and dibenzoindenofluorene-amines and dibenzoindenofluorene-diamines, for example in accordance with WO 2007/140847.

Examples of dopants from the class of the styrylamines are substituted or unsubstituted tristilbene-amines or the dopants described in WO 2006/000388, WO 2006/058737, WO 2006/

000389, WO 2007/065549 and WO 2007/115610. Distyrylbenzene and distyrylbiphenyl derivatives are described in U.S. Pat. No. 5,121,029. Further styrylamines are found in US 2007/0122656 A1. Particularly preferred styrylamine dopants and triarylamine dopants are the compounds of the Formulae (1) to (6) and as disclosed in U.S. Pat. No. 7,250,532 B2, DE 102005058557 A1, CN 1583691 A, JP 08053397 A, U.S. Pat. No. 6,251,531 B1, and US 2006/210830 A.

Formula (1)

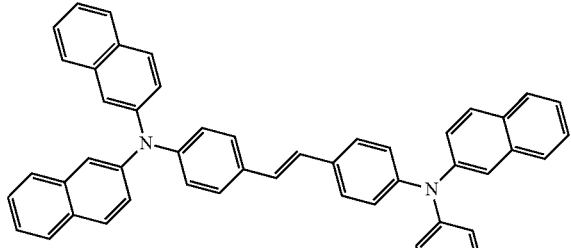

Formula (2)

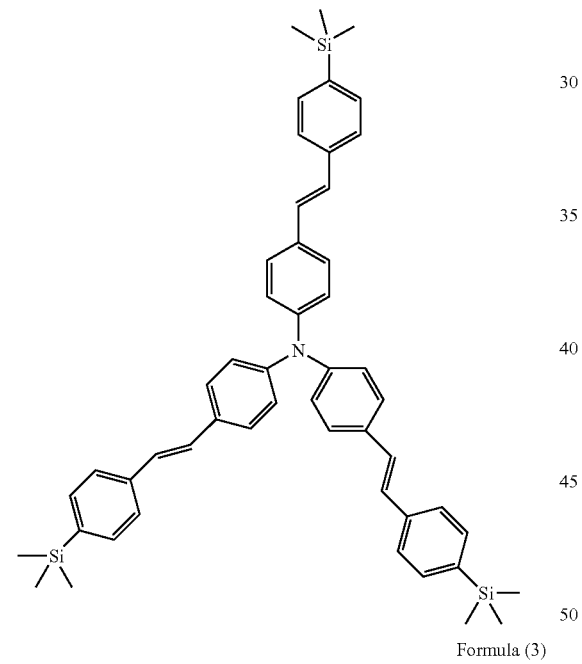

Formula (3)

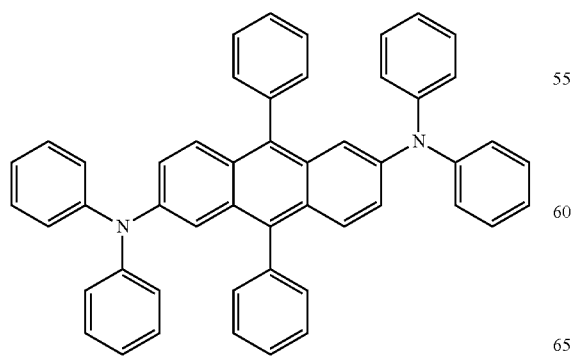

Formula (4)

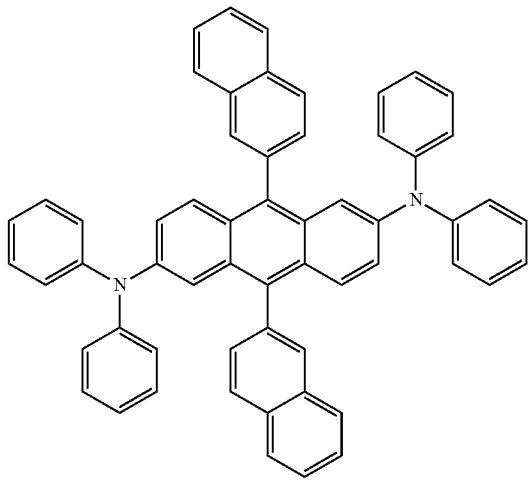

Formula (5)

Formula (6)

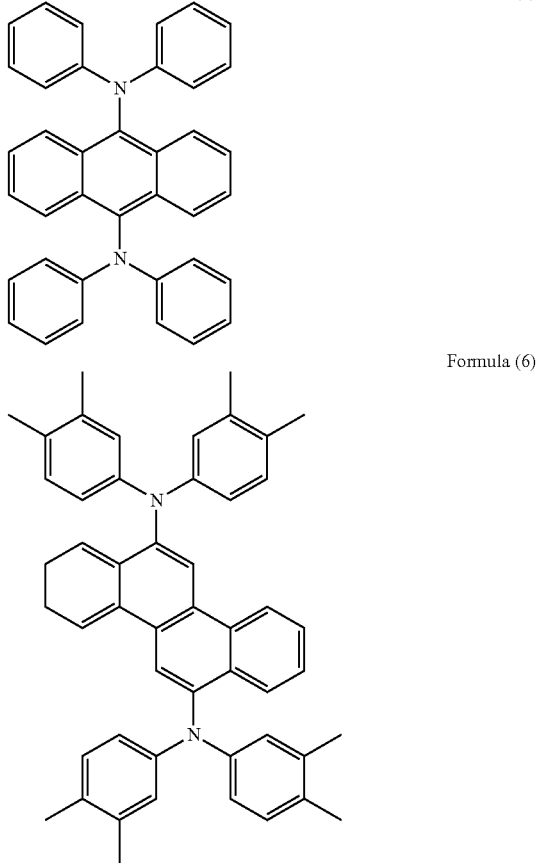

Further preferred fluorescent dopants are selected from the group of triarylamines as disclosed in EP 1957606 A1 and US 2008/0113101 A1.

Further preferred fluorescent dopants are selected from derivatives of naphthalene, anthracene, tetracene, fluorene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. No. 4,769,292, U.S. Pat. No. 6,020,078, US 2007/0252517 A1), pyran, oxazone, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)-benzene is also a preferred dopant.

Preferred host materials suitable for fluorescent emitter are selected from anthracenes, benzanthracenes, indenofluorenes, indenocarbazoles, indolocarbazoles, fluorenes, spirobifluorenes, phenanthrenes, dehydrophenanthrenes, thiophenes, triazines, imidazole and derivatives thereof.

Preferred host materials suitable for fluorescent emitter are selected from anthracenes, benzanthracenes, indenofluorenes, indenocarbazoles, indolocarbazoles, fluorenes, spirobifluorenes, phenanthrenes, dehydrophenanthrenes, thiophenes, triazines, and imidazole.

Particularly preferred host materials for fluorescent emitter are selected from the classes of the oligoarylenes (for example 2,2',7,7'-tetraphenyl-spirobifluorene in accordance with EP 676461 or dinaphthylanthracene), in particular the oligoarylenes containing condensed aromatic groups, such as, for example, phenanthrene, tetracene, coronene, chrysene, fluorene, spirofluorene, perylene, phthaloperylene, naphthaloperylene, decacyclene, rubrene, the oligoarylenevinylenes (for example 4,4'-bis(2,2-diphenylethenyl)-1,1'-biphenyl (DPVBi) or 4,4-bis-2,2-diphenylvinyl-1,1-spirobi-phenyl (spiro-DPVBi) in accordance with EP 676461), the polypodal metal complexes (for example in accordance with WO 2004/081017), in particular metal complexes of 8 hydroxyquinoline, for example aluminium(III) tris(8-hydroxyquinoline) (aluminium quinolate, $Alq_3$) or bis(2-methyl-8-quinolinolato)-4-(phenylphenolinolato)aluminium, also with imidazole chelate (US 2007/0092753 A1) and quinoline-metal complexes, aminoquinoline-metal complexes, benzoquinoline-metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (e.g. DE 102007024850). Particularly preferred host materials are selected from the classes of the oligoarylenes, containing naphthalene, anthracene, benzanthracene and/or pyrene, or atropisomers of these compounds, the ketones, the phosphine oxides and the sulfoxides. Very particularly preferred host materials are selected from the classes of the oligoarylenes, containing anthracene, benzanthracene and/or pyrene, or atropisomers of these compounds. For the purposes of this invention, an oligoarylene is intended to be taken to mean a compound in which at least three aryl or arylene groups are bonded to one another.

Further preferred host materials for fluorescent emitter are selected, in particular, from compounds of the Formula (7)

$$Ar^4—(Ar^5)_p—Ar^6 \quad \text{Formula (7)}$$

wherein
$Ar^4$, $Ar^5$, $Ar^6$ are on each occurrence, identically or differently, an aryl or heteroaryl group having 5 to 30 aromatic ring atoms, which may be substituted by one or more radicals and p is 1, 2, or 3, the sum of the π-electrons in $Ar^4$, $Ar^5$ and $Ar^6$ is at least 30 if p=1 and is at least 36 if p=2 and is at least 42 if p=3.

It is particularly preferred in the host materials of the Formula (7) for the group $Ar^5$ to stand for anthracene, which may be substituted by one or more radicals $R^1$, and for the groups $Ar^4$ and $Ar^6$ to be bonded in the 9 and 10-positions. Very particularly preferably, at least one of the groups $Ar^4$ and/or $Ar^6$ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals $R^1$. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)anthracene and 9,10-bis[4-(2,2-diphenylethenyl)phenyl]anthracene, 9,10-diphenylanthracene, 9,10-bis(phenylethynyl)anthracene and 1,4-bis(9'-ethynylanthracenyl)benzene. Preference is also given to host materials containing two anthracene units (US 2008/0193796 A1), for example 10,10'-bis[1,1',4',1"]terphenyl-2-yl-9,9'-bisanthracenyl.

Further preferred host materials are derivatives of arylamine, styrylamine, fluorescein, perynone, phthaloperynone, naphthaloperynone, diphenylbutadiene, tetraphenylbutadiene, cyclopentadienes, tetraphenylcyclopentadiene, pentaphenylcyclopentadiene, coumarine, oxadiazole, bisbenzoxazoline, oxazone, pyridine, pyrazine, imine, benzothiazole, benzoxazole, benzimidazole (US 2007/0092753 A1), for example 2,2',2"-(1,3,5-phenylene)tris[1-phenyl-1H-benzimidazole], aldazines, stilbene, styrylarylene derivatives, for example 9,10-bis[4-(2,2-diphenylethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, mellocyanine, acridone, quinacridone, cinnamic acid esters and fluorescent dyes.

Particular preference is given to derivatives of arylamine and styrylamine, for example 4,4'-bis[N-(1-naphthyl)-N-(2-naphthyl)amino]biphenyl (TNB).

Preferred compounds with oligoarylene as hosts for fluorescent emitter are compounds as disclosed in, e.g., US 2003/0027016 A1, U.S. Pat. No. 7,326,371 B2, US 2006/043858 A, U.S. Pat. No. 7,326,371 B2, US 2003/0027016 A1, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678, and US 2007/0205412 A1. Particularly preferred oligoarylene-based compounds are compounds having the Formulae (8) to (14).

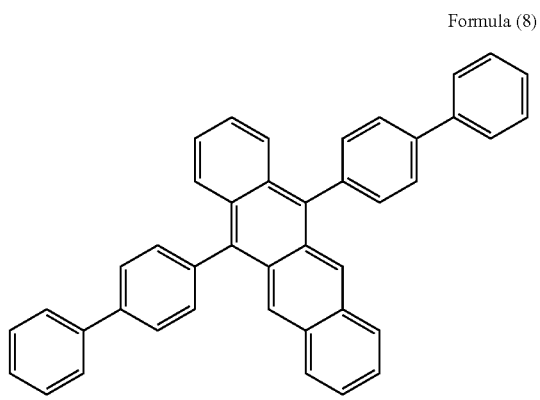

Formula (8)

Formula (9)

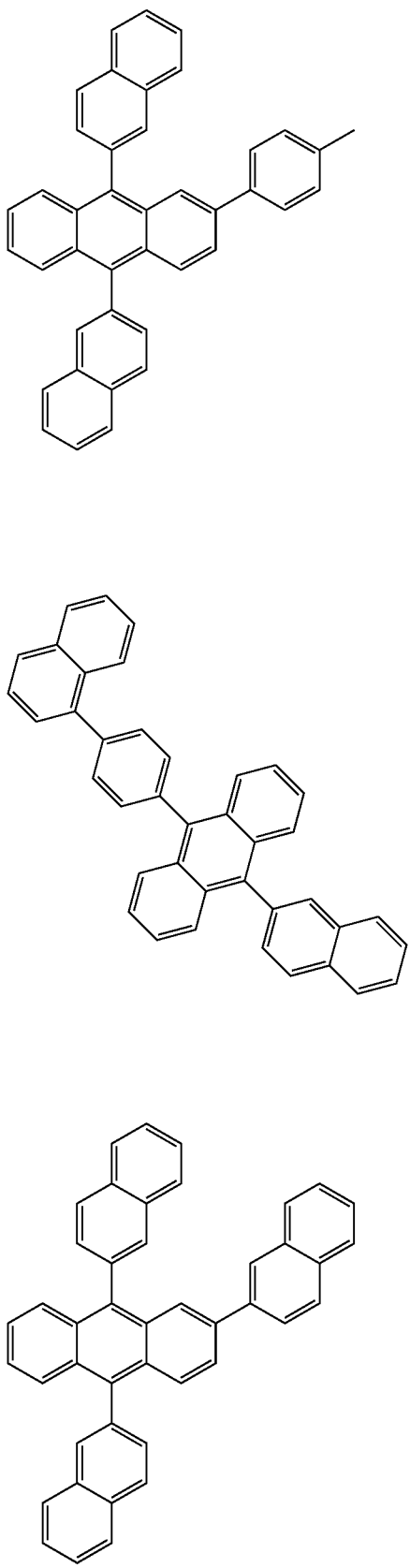

Formula (10)

Formula (11)

Formula (12)
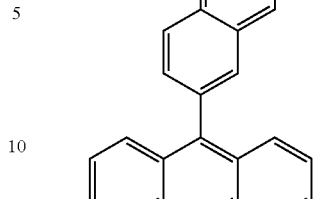

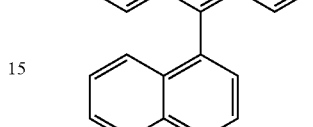

Formula (13)
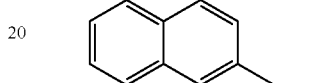

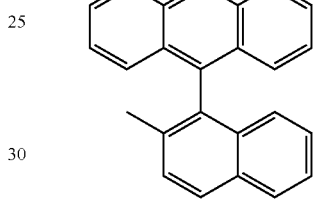

Formula (14)

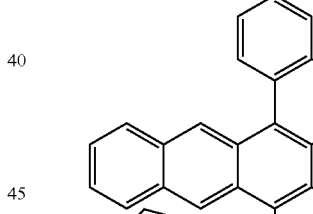

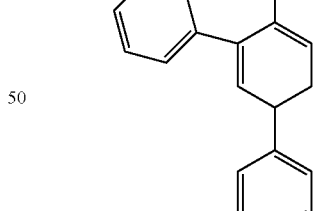

Further host materials for fluorescent emitter can be selected from spirobifluorene and derivates thereof, for example Spiro-DPVBi as disclosed in EP 0676461 and indenofluorene as disclosed in U.S. Pat. No. 6,562,485.

In another very preferred embodiment, EL-F comprises in the emissive layer one nanocrystal, one organic phosphorescent emitter and one host material. The suitable phosphorescent emitter and host materials for such combination is described below.

Examples of phosphorescent emitters are revealed by the applications WO 00/70655, WO 01/41512, WO 02/02714, WO 02/15645, EP 1191613, EP 1191612, EP 1191614 and WO 2005/033244. In general, all phosphorescent complexes as used in accordance with the prior art for phosphorescent compounds used in electroluminescent devices and as are known to the person skilled in the art in the area of organic electroluminescence are suitable, and the person skilled in the art will be able to use further phosphorescent complexes without inventive step.

The phosphorescent emitter may be a metal complex, preferably with the formula $M(L)_z$, wherein M is a metal atom, L is in each occurrence independently of one another an organic ligand that is bonded to or coordinated with M via one, two or more positions, and z is an integer≥1, preferably 1, 2, 3, 4, 5 or 6, and wherein, optionally, these groups are linked to a polymer via one or more, preferably one, two or three positions, preferably via the ligands L.

M is in particular a metal atom selected from transition metals, preferably selected from transition metals of group VIII, or lanthanoides, or actinides, particularly preferably selected from Rh, Os, Ir, Pt, Pd, Au, Sm, Eu, Gd, Tb, Dy, Re, Cu, Zn, W, Mo, Pd, Ag, or Ru, and very particularly preferably selected from Os, Ir, Ru, Rh, Re, Pd, or Pt. M may also be Zn.

The EL-F according to the present invention preferably comprises at least one emissive metal complex. According to quantum mechanics the transition from excited states with high spin multiplicity, e.g. from excited triplet states, to ground state is forbidden. However, the existence of an heavy atom, for example iridium, osmium, platinum and europium, results in a strong spin-orbit coupling, i.e. the excited singlet and triplet are mixed so that triplet gains some singlet character; and if singlet-triplet mixing yields a radiative decay rate faster than the non-radiative event, then the luminance can be efficient. This kind of emission can be achieved using metal complex, as firstly reported by Baldo et al.; Nature 395, 151-154 (1998).

Preferred ligands are 2 phenylpyridine derivatives, 7,8-benzoquinoline derivatives, 2 (2-thienyl)pyridine derivatives, 2 (1-naphthyl)pyridine derivatives or 2 phenylquinoline derivatives. All these compounds may be substituted, for example by fluoro- or trifluoromethyl substituents for blue emission. Auxiliary ligands are preferably acetylacetonate or picric acid.

In particular, complexes of Pt or Pd with tetradentate ligands of the Formula (15) as disclosed in US 2007/0087219 A1, wherein $R^1$ to $R^{14}$ and $Z^1$ to $Z^5$ are as defined in the reference, Pt porphyrin complexes having an enlarged ring system (US 2009/0061681 A1) and Ir complexes are suitable, for example 2,3,7,8,12,13,17,18-octaethyl-21H, 23H-porphyrin-Pt(II), tetraphenyl-Pt(II)-tetrabenzoporphyrin (US 2009/0061681 A1), cis-bis(2-phenylpyridinato-N,C2')Pt(II), cis-bis(2-(2'-thienyl)pyridinato-N,C3')Pt(II), cis-bis(2-(2'-thienyl)quinolinato-N,C5')Pt(II), (2-(4,6-difluoro-phenyl)pyridinato-N,C2')Pt(II) acetylacetonate, or tris(2-phenylpyridinato-N,C2')Ir(III) (Ir(ppy)₃, green), bis(2-phenylpyridinato-N,C2)Ir(III) acetylacetonate (Ir(ppy)₂ acetylacetonate, green, US 2001/0053462 A1, Baldo, Thompson et al. Nature 403, (2000), 750-753), bis(1-phenyl-isoquinolinato-N,C2')(2-phenylpyridinato-N,C2')iridium (III), bis(2-phenylpyridinato-N,C2')(1-phenylisoquinolinato-N,C2')iridium(III), bis(2-(2'-benzothienyl)-pyridinato-N,C3')iridium(III) acetylacetonate, bis(2-(4',6'-difluorophenyl)-pyridinato-N,C2')iridium(III) piccolinate (Firpic, blue), bis(2-(4',6'-difluoro-phenyl)pyridinato-N,C2') Ir(III) tetrakis(1-pyrazolyl)borate, tris(2-(biphenyl-3-yl)-4-tert-butylpyridine)iridium(III), (ppz)₂Ir(5phdpym) (US 2009/0061681 A1), (45ooppz)₂Ir(5phdpym) (US 2009/0061681 A1), derivatives of 2 phenylpyridine-Ir complexes, such as, for example, iridium(III) bis(2-phenylquinolyl-N, C2')acetylacetonate (PQIr), tris(2-phenylisoquinolinato-N, C)Ir(III) (red), bis(2-(2'-benzo[4,5-a]thienyl)pyridinato-N, C3)Ir acetylacetonate ([Btp2Ir(acac)], red, Adachi et al. Appl. Phys. Lett. 78 (2001), 1622-1624).

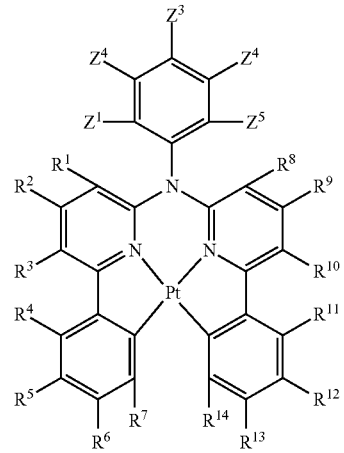

Formula (15)

Also suitable are complexes of trivalent lanthanides, such as, for example, $Tb^{3+}$ and $Eu^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JACS 105, 1983, 1795), Re(I) tricarbonyl diimine complexes (Wrighton, JACS 96, 1974, 998 inter alia), Os(II) complexes with cyano ligands and bipyridyl or phenanthroline ligands (Ma et al., Synth. Metals 94, 1998, 245) or $Alq_3$ without a host.

Further phosphorescent emitters with tridentate ligands are described in U.S. Pat. No. 6,824,895 and U.S. Pat. No. 7,029,766. Red-emitting phosphorescent complexes are mentioned in U.S. Pat. No. 6,835,469 and U.S. Pat. No. 6,830,828.

A particularly preferred phosphorescent dopant is a compound with the Formula (16) and further compounds as disclosed, e.g., in US 2001/0053462 A1.

A particularly preferred phosphorescent dopant is a compound with the Formula (17) and further compounds as disclosed, e.g., in WO 2007/095118 A1

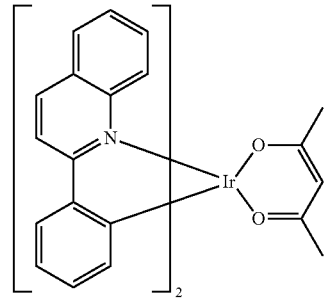

Formula (16)

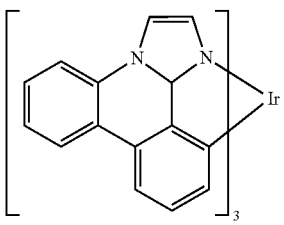

Formula (17)

Further derivatives are described in U.S. Pat. No. 7,378,162 B2, U.S. Pat. No. 6,835,469 B2, and JP 2003/253145 A.

Further preference is given to phosphorescent emitter selected from carbene triple emitter, particularly to carbine complexes comprising iridium as metal. Preferred complexes are N-heterocyclic carbine (NHC) iridium complexes as disclosed in WO 2005/091373, WO 2005/113704, and in P. Erk et al., SID 2006, 11, 2, 131, e.g. fac-Ir(dpbic)$_3$, Ir(pmbic)$_3$, Ir(pmic)$_3$, Ir(dpnic)$_3$, Ir(cn-pmic)$_3$.

Further to metal complex mentioned elsewhere herein, a suitable metal complex according to the present invention can be selected from transition metals, rare earth elements, lanthanides and actinides is also subject of this invention. Preferably the metal is selected from Ir, Ru, Os, Eu, Au, Pt, Cu, Zn, Mo, W, Rh, Pd, or Ag.

The preferred host materials for phosphorescent emitter, i.e. matrix materials, are selected from ketones, carbazoles, indolocarbazoles, triarylamines, indenofluorenes, fluorenes, spirobifluorenes, phenathrenes, dehydrophenanthrenes, thiophenes, triazines, imidazoles and their derivatives. Some preferred derivatives are described below in more details.

If a phosphorescent emitter is employed the host material must fulfil rather different characteristics as compared to host materials used for fluorescent emitter. The host materials used for phosphorescent emitter are required to have a triplet level which is higher in energy as compared to the triplet level of the emitter. The host material can either transport electrons or holes or both of them. In addition, the emitter is supposed to have large spin-orbital coupling constants in order to facilitate singlet-triplet mixing sufficiently. This can be enabled by using metal complexes.

Preferred matrix materials are N,N-biscarbazolylbiphenyl (CBP), carbazole derivatives (for example in accordance with WO 2005/039246, US 2005/0069729, JP 2004/288381, EP 1205527 or DE 102007002714), azacarbazoles (for example in accordance with EP 1617710, EP 1617711, EP 1731584, JP 2005/347160), ketones (for example in accordance with WO 2004/093207), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (e.g. in accordance with DE 102008017591), azaboroles or boronic esters (for example in accordance with WO 2006/117052), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, indoles, anthrone derivatives, fluorenone derivatives, fluorenylidenemethane derivatives, hydrazone derivatives, silazane derivatives, aromatic dimethylidene compounds, porphyrin compounds, carbodiimide derivatives, diphenylquinone derivatives, phthalocyanine derivatives, metal complexes of 8 hydroxyquinoline derivatives, such as, for example, Alq$_3$, the 8 hydroxyquinoline complexes may also contain triarylaminophenol ligands (US 2007/0134514 A1), various metal complex-polysilane compounds with metal phthalocyanine, benzoxazole or benzothiazole as ligand, hole-conducting polymers, such as, for example, poly(N-vinylcarbazole) (PVK), aniline copolymers, thiophene oligomers, polythiophenes, polythiophene derivatives, polyphenylene derivatives, polyfluorene derivatives.

Further particularly preferred matrix materials are selected from compounds comprising indolocarbazoles and their derivatives (e.g. Formulae (18) to (24), as disclosed for examples in DE 102009023155.2, EP 0906947B1, EP 0908787B1, EP 906948B1, WO 2008/056746A1, WO 2007/063754A1, WO 2008/146839A1, and WO 2008/149691A1.

Formula (18)

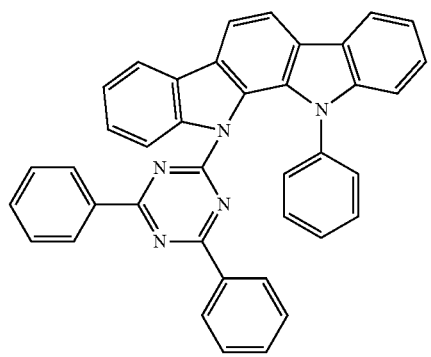

Formula (19)

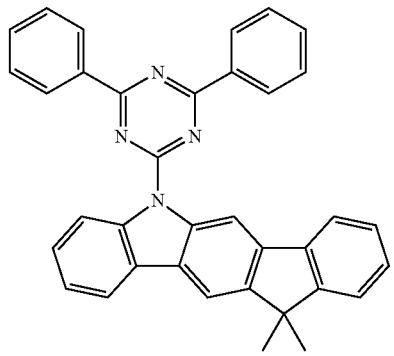

Formula (20)

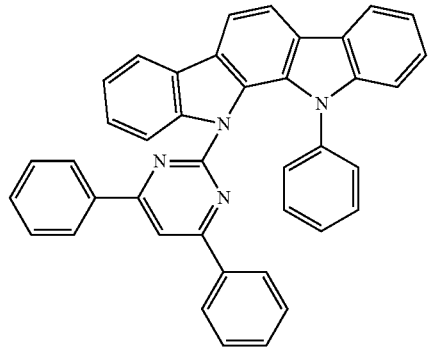

-continued

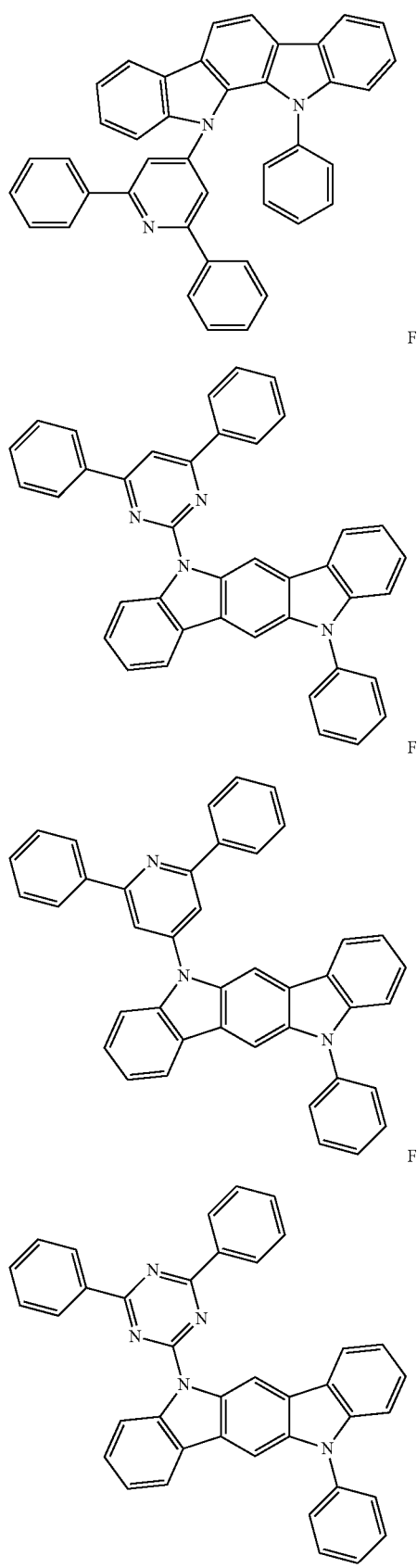

Formula (21)

Formula (22)

Formula (23)

Formula (24)

Examples of preferred carbazole derivatives are, 1,3-N,N-dicarbazolebenzene (=9,9'-(1,3-phenylene)bis-9H-carbazole) (mCP), 9,9'-(2,2'-dimethyl[1,1'-biphenyl]-4,4'-diyl) bis-9H-carbazole (CDBP), 1,3-bis(N,N'-dicarbazole) benzene (=1,3-bis(carbazol-9-yl)benzene), PVK (polyvinylcarbazole), 3,5-di(9H-carbazol-9-yl)biphenyl and compounds of the Formulae (25) to (29).

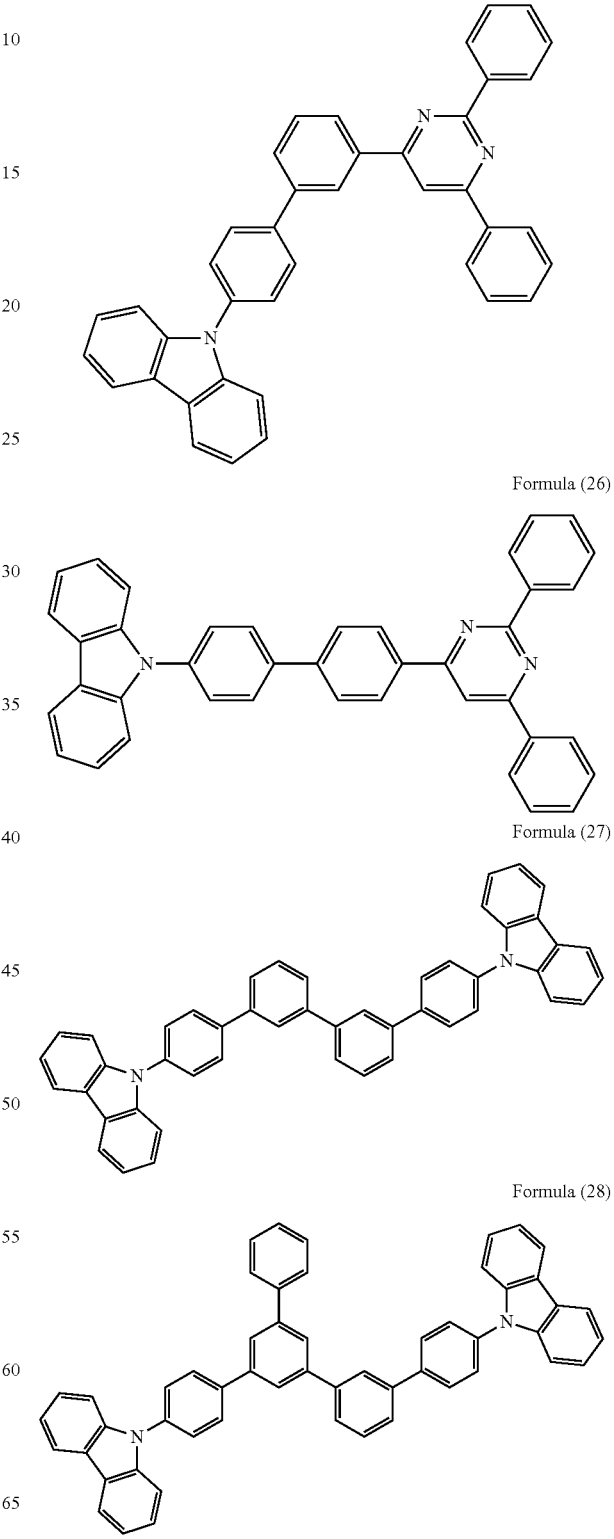

Formula (25)

Formula (26)

Formula (27)

Formula (28)

-continued

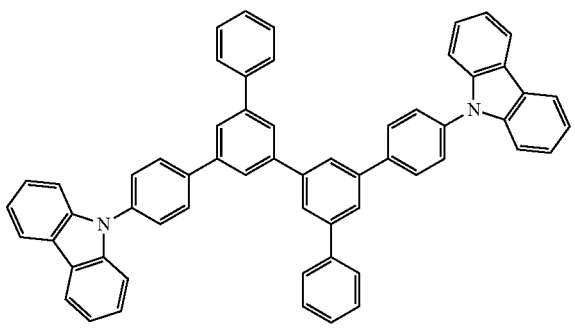

Formula (29)

Preferred Si tetraaryl compounds are, for example, (US 2004/0209115, US 2004/0209116, US 2007/0087219 A1, US 2007/0087219 A1) the compounds of the Formulae (30) to (35).

Formula (30)

Formula (31)

Formula (32)

Formula (33)

-continued

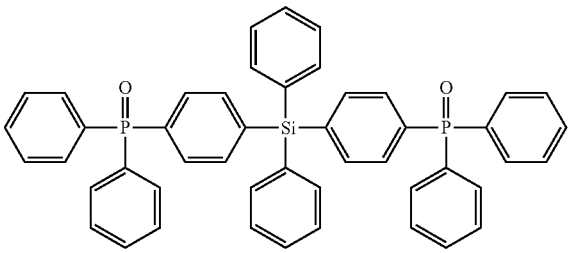

Formula (34)

Formula (35)

A particularly preferred matrix for phosphorescent dopants is the compound of Formula (36) (EP 652273 B1)

Formula (36)

Further particularly preferred matrix materials for phosphorescent dopants are selected from compounds of the general Formula (37) (EP 1923448A1).

[M(L)$_2$]$_n$    Formula (37)

wherein M, L, and n are defined as in the reference. Preferably M is Zn, and L is quinolinate, and n is 2, 3 or 4. Very particularly preferred are [Znq$_2$]$_2$, [Znq$_2$]$_3$, and [Znq$_2$]$_4$.

Preference is given to co-hosts selected from metal oxinoid complexes whereby lithium quinolate (Liq) or Alq$_3$ are particularly preferred.

In yet another preferred embodiment, EL-F comprises in the emissive layer one nanocrystal, one organic emissive compound, which is a polymer, oligomer, dendrimer, and blend.

The polymer may also have further functions such as charge transfer transport function.

Preferably, the said polymer comprises units, which are preferably selected from the groups comprising phosphorescent emitter, particularly emissive metal complexes as described above. Particular preference is given here to corresponding structural units which contain elements from groups 8 to 10 (Ru, Os, Rh, Ir, Pd, Pt).

The polymer is characterized in that different functions may be incorporated into one large molecule or a blend of large molecules. The functions are, inter alia, the ones of a hole injection material, hole transport material, emissive material, electron injection material, and electron transport material. The functions which are incorporated into a polymer can be categorized into different groups. By choosing the desired functional groups and the ratio between them, the polymer can be tuned to have the desired function(s).

The difference between polymers, oligomers and dendrimers is due to the size, size distribution, and branching of the molecular entities as defined elsewhere within the present invention.

Different structures are, inter alia, those as disclosed and extensively listed in WO 2002/077060 A1 and in DE 10337346 A1. The structural units may originate, for example, from the following groups:

Group 1: units which increase the hole-injection and/or transport properties of the polymers; It corresponds to the HIMs or HTMs as described elsewhere within the present invention.
Group 2: units which increase the electron-injection and/or transport properties of the polymers; It corresponds to the EIMs or ETMs as described elsewhere within the present invention.
Group 3: units which have combinations of individual units from group 1 and group 2;
Group 4: units which modify the emission characteristics to such an extent that electrophosphorescence may be obtained instead of electrofluorescence; typically, it corresponds to the phosphorescent emitter, or more preferably emissive metal complexes as described elsewhere within the present invention.
Group 5: units which improve the transition from the so called singlet state to higher spin states, e.g. to a triplet state;
Group 6: units which influence the morphology and/or emission colour of the resultant polymers;
Group 7: units which are typically used as backbone and which may have electron transport function, hole transport function or both.

The fiber according to the present invention may further comprise one or more additional functional layer selected from hole transport layer (HTL), hole injection layer (HIL), electron transport layer (ETL), and electron injection layer (EIL), electron blocking layer (EBL), and hole blocking layer (HBL). The said functional layer comprises at least one corresponding functional material, i.e., HTL comprises at least one HTM, HIM at least one HIM, ETL at least one ETM, EIL at least one EIM, EBL at least one EBM, and HBL at least one HBM.

The suitable functional materials, incl. HTM, HIM, HBM, ETM, EIM and EBM are known to the skilled one in the field of OLEDs (as disclosed, e.g., in WO 2011/015265).

The fiber according to the present invention comprises at least one semiconductor nanocrystal, which is preferably emissive.

A nanocrystal is a nanometer sized particle, e.g., in the size range of up to about 1000 nm. In a preferred embodiment of the present invention, the nanocrystal can have a size in the range of up to about 100 nm. In a very preferred embodiment, the nanocrystal can have a size in the range up to about 20 nm (such as about 1, 2, 3, 4, 5, 6, 7, 8, 9, 10, 11, 12, 13, 14, 15, 16, 17, 18, 19, or 20 nm). In certain embodiments, the nanocrystal can have a size less than 100 A. In another very preferred embodiment, a nanocrystal has a size in a range from about 1 to about 6 nanometers and more particularly from about 1 to about 5 nm.

Suitable nanocrystals can have various shapes. Examples of the shape of a nanocrystal include, but are not limited to, sphere, rod, disk, tetrapod, other shapes, and/or mixtures thereof.

The suitable semiconductor nanocrystal can further include an overcoating or shell over at least a portion of, and preferably all of, the outer surface of the semiconductor nanocrystal. In certain embodiments, the shell comprises one or more semiconductor materials. In certain embodiments, the one or more additional semiconductor materials in the shell are different from the semiconductor material included in the nanocrystal core. In certain embodiments, a shell can comprise two or more layers of the same or different semiconductor materials. In certain embodiments, a layer can include a single semiconductor material or a mixture of two or more semiconductor materials with different compositions, particle sizes, and/or emission characteristics. A semiconductor material may comprise a compound, a doped compound, and/or an alloy. A nanocrystal core surrounded by a shell is also referred to as having a "core/shell" structure.

In a preferred embodiment, the semiconductor nanocrystals have a narrow size distribution, the so-called mono-dispersive distribution of size. The monodisperse distribution of particles can also be referred to as a size. Preferably, a mono-disperse population of particles includes a population of particles wherein at least about 60% of the particles in the population fall within a specified particle size range. A population of monodisperse particles preferably deviate less than 15% rms (root-mean-square) in particle size and more preferably less than 10% rms and most preferably less than 5%.

Transmission electron microscopy (TEM) can be used to get information about the size, shape, and distribution of the nanocrystals. Powder X-ray diffraction (XRD) patterns can provide the most complete information regarding the type and quality of the crystal structure of the nanocrystals. Particle size can be estimated because it is inversely related, via the X-ray coherence length, to the peak width. For example, the diameter of the nanocrystals can be measured directly by transmission electron microscopy or estimated from X-ray diffraction data using, for example, the Scherrer equation. It also can be estimated from the UV/Vis absorption spectrum. Analytic methods are also developed to determine the size distribution of nanocrystals, for example Analytical ultracentrifugation (AUC) as reported by by Lees et al., in Nano Lett., 2008, 8 (9), pp 2883-2890. More on characterisation methods can be referred to Anal. Chem., 2011, 83 (12), pp 4453-4488. In the present invention, TEM and XRD were used to characterise the nanocrystals.

The suitable semiconductor nanocrystal can comprise semiconductor selected from Group II-VI, Group III-V, Group IV-VI and Group IV semiconductors, preferably from ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination thereof.

In a particularly preferred embodiment, the nanocrystal is the mono-dispersive spherical nanocrystal, hereafter also called quantum dot (QD).

The advantages of QDs are: 1) theoretical internal quantum efficiency as high as 100%, compared to 25% of the singlet organic emitter; 2) soluble in common organic solvents; 3) emission wavelength can be easily tuned by the core size; 4) narrow emission spectrum; 5) intrinsic stability in inorganic materials.

Quantum dots can easily be produced and have a narrow emission spectrum in contrast to organic fluorescent or phosphorescent compounds. They can be tailored in terms of size which determines the QD's emission maximum. High photoluminescent efficiency can also be obtained with quantum dots. Furthermore their emission intensity can be tailored by their concentration employed. Moreover, QDs are soluble in many solvents or can easily be made soluble in common organic solvents, allowing versatile processing methods, particularly printing methods such as screen printing, off-set printing, and ink jet printing.

In general, a QD is a semiconductor whose excitons are confined in all three spatial dimensions. As a result, they have properties that are between those of bulk semiconductors and those of discrete molecules. There are several ways to prepare QD structures, for example by chemical methods or by ion implantation, or in nanodevices made by state-of-the-art lithographic techniques.

The quatuim dots of the present invention refer to colloidal semiconductor nanocrystals, also known as colloidal quantum dots, or nanodots or nanocrystals, which are produced by chemical methods.

The first mono-dispersive colloidal quantum dots including a semiconducting material were based on CdE (E=S, Se, Te) and were produced using the so called TOPO (trioctyl phosphine oxide) method by Bawendi and later modified by Katari et al. A review on synthesis of QDs is given by Murray, Norris and Bawendi, "Synthesis and characterization of nearly monodisperse CdE (E=sulfur, selen, tellurium) semiconductor nanocrystallites", J. Am. Chem. Soc. 115[19], 8706-8715, 1993. While any method known to the skilled person can be used to create QDs, preferably a solution-phase colloidal method for controlled growth of inorganic QDs is used. The said colloidal methods are disclosed, e.g., by Alivisatos, A. P., "Semiconductor clusters, nanocrystals, and quantum dots," Science 271:933 (1996); X. Peng, M. Schlamp, A. Kadavanich, A. P. Alivisatos, "Epitaxial growth of highly luminescent CdSe/CdS Core/Shell nanocrystals with photostability and electronic accessibility," J. Am. Chem. Soc. 30:7019-7029 (1997); and C. B. Murray, D. J. Norris, M. G. Bawendi, "Synthesis and characterization of nearly monodisperse CdE (E=sulfur, selenium, tellurium) semiconductor nanocrystallites," J. Am. Chem. Soc. 115:8706 (1993). These methods allow low cost processability without the need for clean rooms and expensive manufacturing equipment. In these methods, metal precursors that undergo pyrolysis at high temperature are rapidly injected into a hot solution of organic surfactant molecules. These precursors break apart at high temperatures and react to nucleate nanocrystals. After this initial nucleation phase, a growth phase begins by the addition of monomers to the growing crystal. Thus, crystalline nanoparticles are obtained in solution that has an organic surfactant molecule coating their surface.

In these methods, synthesis occurs as an initial nucleation event that takes place over seconds, followed by crystal growth at elevated temperature for several minutes. Parameters such as the temperature, types of surfactants present, precursor materials, and ratios of surfactants to monomers can be modified so as to change the nature and progress of the reaction. The temperature controls the structural phase of the nucleation event, rate of decomposition of precursors, and rate of growth. The organic surfactant molecules mediate both solubility and control of the nanocrystal shape. The ratio of surfactants to monomer, surfactants to each other, monomers to each other, and the individual concentrations of monomers strongly influence the kinetics of growth.

The EL-F according to the present invention preferably comprise the QD(s) in each a concentration of at least 0.1 wt %, particularly preferably at least 0.5 wt %, and very particularly preferably of at least 3 wt % with respect to the total amount of the emissive layer.

In one embodiment the EL-F according to the present invention comprises less than 15, preferably less than 10, particularly preferably less than 7, and very particularly preferably less than 5 small organic functional material(s).

In principle any QD known to one skilled in the art can be employed in EL-F according to the present invention Preference is given to QDs having emission intensity maxima in the range between 300 and 2000 nm, preferably between 350 and 1500 nm. Emission wavelengths can easily be adjusted by choosing the suitable organic semiconductor and/or by choosing the suitable quantum dot and/or by the size of a quantum dot, which in turn can precisely be tailored by synthesis. Intensities of emission can also be adapted by the concentration of a specifically sized QD used in the said EL-F.

Preferably the EL-F according to the present invention comprises quantum dots selected from Group II-VI, Group III-V, Group IV-VI and Group IV semiconductors, preferably ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination thereof.

Suitable semiconducting materials, which can be incoporated into QDs, are selected from elements of Group II-VI, such as CdSe, CdS, CdTe, ZnSe, ZnO, ZnS, ZnTe, HgS, HgSe, HgTe and alloys thereof such as CdZnSe; Group III-V, such as InAs, InP, GaAs, GaP, InN, GaN, InSb, GaSb, AlP, AlAs, AlSb and alloys such as InAsP, CdSeTe, ZnCdSe, InGaAs; Group IV-VI, such as PbSe, PbTe and PbS and alloys thereof; Group III-VI, such as InSe, InTe, InS, GaSe and alloys such as InGaSe, InSeS; Group IV semiconductors, such as Si and Ge alloys thereof, and combinations thereof in composite structures.

Further suitable semiconductor materials include those disclosed in U.S. patent application Ser. No. 10/796,832 and include any type of semiconductor, including group II-VI, group III-V, group IV-VI and group IV semiconductors. Suitable semiconductor materials include, but are not limited to, Si, Ge, Sn, Se, Te, B, C (including diamond), P, BN, BP, BAs, AlN, AlP, AlAs, AlS, AlSb, BaS, BaSe, BaTe, CaS, CaSe, CaTe, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and an appropriate combination of two or more such semiconductors.

Preferably the QD is selected from Group II-VI, Group III-V, Group IV-VI and Group IV semiconductors, particularly preferably from ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination thereof.

In some embodiments, the quantum dots may comprise a dopant from the group consisting of: a p-type dopant or an n-type dopant. The properties and synthesis of a doped quantum dot can be referred to "n-type colloidal semiconductor nanocrystals" by Moonsub Shim & Philippe Guyot-Sionnest, Nature vol 407 (2000) p 981, and "Doped Nanocrystals" by Norris et al., Science, 319 (2008), p 1776. The quantum dots of the present invention can also comprise II-VI or III-V semiconductors. Examples of II-VI or III-V semiconductor nanocrystals include any combination of an element from Group II, such as Zn, Cd and Hg, with any element from Group VI, such as S, Se, Te, Po, of the Periodic Table; and any combination of an element from Group III, such as B, Al, Ga, In, and Tl, with any element from Group V, such as N, P, As, Sb and Bi, of the Periodic Table.

In quantum dots, photoluminescence and electroluminescence arise from the band edge states of the nanocrystal. The radiative band-edge emission from nanocrystals competes with non-radiative decay channel originating from surface electronic states, as reported by X. Peng, et al., J. Am. Chem. Soc. Vol 119:7019-7029 (1997). Thus, the presence of surface defects such as dangling bonds provides non-radiative recombination centers and lower emission efficiency. An efficient method to passivate and remove the surface trap states is to epitaxially grow an inorganic shell material on the surface of the nanocrystal, as dislcosed by X. Peng, et al., J. Am. Chem. Soc. Vol 119:7019-7029 (1997). The shell material can be chosen such that the electronic levels are type I with respect to the core material (e.g., with a larger bandgap to provide a potential step localizing the electron and hole to the core). As a result, the probability of non-radiative recombination can be reduced.

Core-shell structures are obtained by adding organometallic precursors containing the shell materials to a reaction mixture containing the core nanocrystal. In this case, rather than a nucleation-event followed by growth, the cores act as the nuclei, and the shells grow from their surface. The temperature of the reaction is kept low to favour the addition of shell material monomers to the core surface, while preventing independent nucleation of nanocrystals of the shell materials. Surfactants in the reaction mixture are present to direct the controlled growth of shell material and ensure solubility. A uniform and epitaxially grown shell is obtained when there is a low lattice mismatch between the two materials. Additionally, the spherical shape acts to minimize interfacial strain energy from the large radius of curvature, thereby preventing the formation of dislocations that could degrade the optical properties of the nanocrystal system.

In a preferred embodiment, ZnS can be used as the shell material using synthetic processes well known to one skilled in the art.

In a particularly preferred embodiment, the QD of the invention comprises semiconducting materials selected from Group II-VI semiconductors, alloys thereof and core/shell structures made there from. In further embodiments, the Group II-VI semiconductors are CdSe, CdS, CdTe, ZnSe, ZnS, ZnTe, alloys thereof, combinations thereof and core/shell, core multi-shell layered-structures thereof.

In some embodiments, the QDs according to the present invention comprise further ligands conjugated, cooperated, associated or attached to their surface. Suitable ligands include any group known to those skilled in the art, including those disclosed in U.S. Ser. No. 10/656,910 and U.S. 60/578, 236. Use of such ligands can enhance the ability of the quantum dots to incorporate into various solvents and matrix materials, including polymers. Further preferred ligands are such having a "head-body-tail" structure, as disclosed in US 2007/0034833A1, wherein further preferably the "body" has an electron or hole transport function, as disclosed in US 20050109989A1.

The term QD refers to nanocrystals that are substantially mono-dispersive in size. A QD has at least one region or characteristic dimension with a dimension of less than about 500 nm, and down to on the order of less than about 1 nm. The term mono-dispersive means the size distribution is within +−10% of the stated value, for example a mono-dispersive nanocrystals of 100 nm in diameter encompasses a range of sizes from 90 nm or larger to 110 nm or smaller.

Due to the finite size of the QDs, in particular core-shell QDs, they display unique optical properties compared to their bulk counterparts. The emission spectrum is defined by a single Gaussian peak, which arises from the band-edge luminescence. The emission peak location is determined by the core particle size as a direct result of quantum confinement effects. The electronic & optical properties are discussed by Al. L. Efros and M. Rosen in Annu. Rev. Mater. Sci. 2000. 30:475-521.

In another particularly preferred embodiment, the nanocrystal is the mono-dispersive spherical nanorod, hereafter also called nanorod.

Nanorods have very similar optical and electronic properties as quantum dots as described above. Besides, nanorods have some unique properties compared to spherical Quantum Dots, for example polarized photoluminescence as reported by Artemyev et al., in Nano Letters, 2003, 3, 509, and excellent polarised gain medium for lasing as reported by Kazes et al., in Adv. Mater, 2002, 14, 317.

The fiber according to the present invention is preferably a light emitting electrochemical cell (LEC) comprising at least one ionic species in the EML.

Preferably, the said at least one ionic specie is mobile.

The said at least one ionic specie can be a part of the ionic QD or ionic organic compound as described above or below.

In one preferred embodiment, the at least one ionic species is selected from an ionic transition metal complex (iTMC).

One typical iTMC material is reported for example by Rudmann et al., J. Am. Chem. Soc. 2002, 124, 4918-4921 and Rothe et al., Adv. Func. Mater. 2009, 19, 2038-2044. The concentrations of the iTMC in the emissive layer (EML) can be from 1 to 50 wt %, preferably from 5 to 30 wt %, particularly preferably from 10 to 30 wt %, and very particularly preferably from 10 to 20 wt % with respect of the emissive layer.

In another very preferred embodiment, the EL-F according to the present invention comprises a nanocrystal, which is itself an ionic compound.

Suitable ionic nanocrystal is selected from nanocrystals comprising at least one ionic ligand (or cap). The suitable ligand for this embodiment can be preferably selected according to the general Formulae (38) and (39):

[K$^+$][A$^-$-B-D]  Formula (38)

[A$^+$][K$^-$-B-D]  Formula (39)

wherein D is an anchor group, which anchors on the nanocrystal surface, for example a thiol group; and B a simple bond or a spacer, preferably selected from alkyl, alkoxy group; and K$^{+/-}$ and A$^{-/+}$ represent cations and an anions as described above.

The nanocrystal, particularly QD, comprising at least one ionic ligand according to Formula (38) or (39) can be synthesized by ligand exchange as reported for example by Denis Dorokhin, et al (Nanotechnology 2010, 21, 285703). The ligand can, e.g., has the following Formula (40).

Formula (40)

[Structure: triflate anion (CF₃SO₃⁻) with tetraalkylammonium cation bearing a thiol-terminated chain]

Ligand exchange can be realized by mixing the toluene solution of trioctylphosphine oxide (TOPO)-coated core-shell CdSe/ZnS QDs with a toluene solution of ligand with formula (104) under nitrogen flow and with the help of heating for example at 40° C. By controlling the reaction time, different degree of ligand exchange, between TOPO and anion in Formula (40), can be obtained. In a preferred embodiment, only partially exchange is desired, therefore, the reaction time is preferably short, for example shorter than 24 hrs.

In yet another very preferred embodiment, the EML of the EL-F comprises at least one non-functional ionic compound. The said non-functional ionic compound in the present invention means a compound which is not a fluorescence or phosphorescence emitter, not a host, not a hole injecting material, not a hole transporting material, not an electron injecting material or not an electron transporting material. Further the term non-functional also excludes the function as hole and/or electron blocking group/compound. Suitable non-functional ionic compound can be referred to EP 11003921.1.

The suitable ionic compound has the general formula $K^+A^-$, wherein $K^+$ and $A^-$ represent a cation and an anion, respectively.

Preferably the ionic compound is soluble in the same solvent as the QD or the organic functional compound(s). This allows the easy preparation of the device from solution. Typically organic emissive materials are soluble in common organic solvents, such as toluene, anisole, chloroform.

The suitable inorganic cations $K^+$ can be selected from, for example, Li+, $K^+$ (potassium) and $Na^+$. Suitable organic cations $K^+$ can be selected from ammonium-, phosphonium-, thiouronium-, guanidinium cations as shown in Formulae (41) to (45) or heterocyclic cations as shown in Formulae (46) to (73).

Formula (41)

$$R^4-\overset{R^1}{\underset{R^3}{\overset{|}{N^+}}}-R^2$$

Formula (42)

$$R^4-\overset{R^1}{\underset{R^3}{\overset{|}{P^+}}}-R^2$$

Formula (43)

[Structure: thiouronium cation with R⁵–S–C⁺(–NR¹R²)(–NR³R⁴)]

Formula (44)

[Structure: guanidinium cation with three NR₂ groups on central C⁺]

Formula (45)

$$R^1\underset{R^3}{\overset{S^+}{\diagdown}}R^2$$

wherein
$R^1$ to $R^6$ can be, independently from each other, selected from linear or hyperbranched alkyl rests with 1 to 20 C-atoms, linear or hyperbranched alkenyl rests with 2 to 20 C-atoms and one or more non-conjugated double bonds, linear or hyperbranched alkinyl rests with 2 to 20 C-atoms and one or more non-conjugated triple bond, saturated, partly saturated or completely saturated cycloalkyl with 3 to 7 C-atoms, which can further be substituted with alkyl groups having 1 to 6 C-atoms, wherein one or more substituents R may be partly or completely substituted with halogen, particularly with —F and/or —Cl, or partly substituted with —OR', —CN, —C(O)OH, —C(O)NR'₂, —SO₂NR'₂, —SO₂OH, —SO₂X, —NO₂, wherein one or two non adjacent and non α-carbon atoms of $R^1$ to $R^6$ can be substituted with groups selected from —O—, —S—, —S(O)—, —SO₂—, —N⁺R'₂—, —C(O)NR'—, —SO₂NR'—, and —P(O)R'—, wherein R'=H, unsubstituted, partly or completely with —F substituted C1 to C6-alkyl, C3 to C7-cycloalkyl, unsubstituted or substituted phenyl and X=halogen.

In Formula (41) $R^1$ to $R^4$ can be H, with the provision that at least one of the rests $R^1$ to $R^4$ is not H. In Formula (42) $R^1$ to $R^4$ can be H and NR'₂, wherein R' is defined as above. In Formula (43) $R^1$ to $R^5$ can be H. In Formula (44) $R^1$ to $R^6$ can be H, CN, and NR'₂, wherein R' is defined as above.

Formula (46)

[Structure: imidazolium cation with substituents R¹', R²', R²', R²', R⁴']

Formula (47)

[Structure: pyrazolium cation with substituents R¹', R²', R²', R²', R⁴']

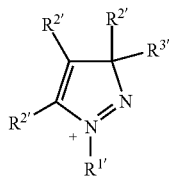
Formula (41)
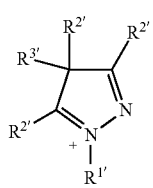
Formula (42)
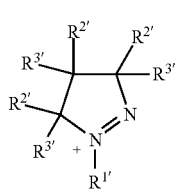
Formula (43)
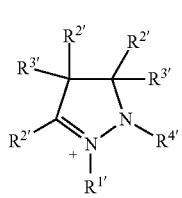
Formula (44)
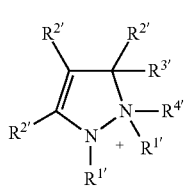
Formula (45)
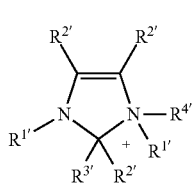
Formula (46)
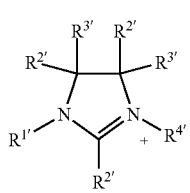
Formula (47)
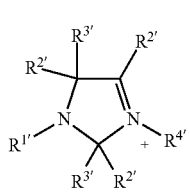
Formula (48)
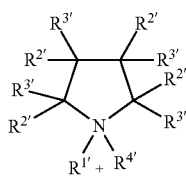
Formula (56)
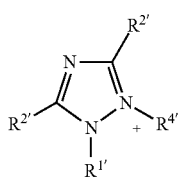
Formula (57)
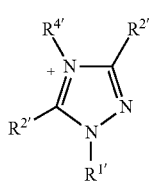
Formula (58)
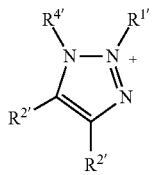
Formula (59)
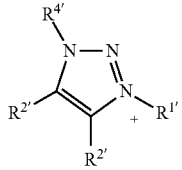
Formula (60)
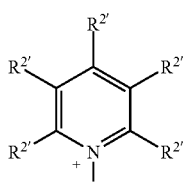
Formula (61)
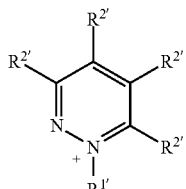
Formula (62)
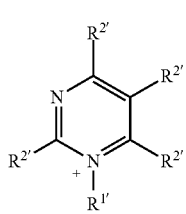
Formula (63)

-continued

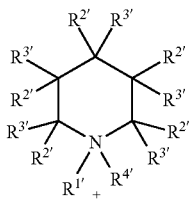
Formula (64)

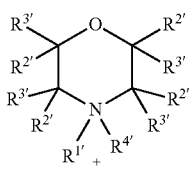
Formula (65)

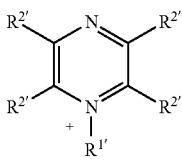
Formula (66)

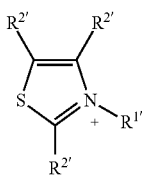
Formula (67)

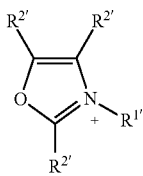
Formula (68)

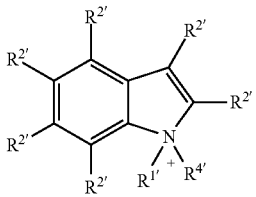
Formula (69)

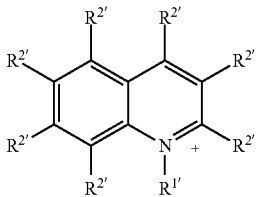
Formula (70)

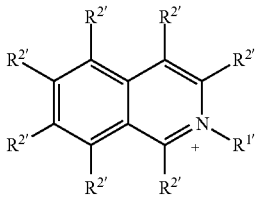
Formula (71)

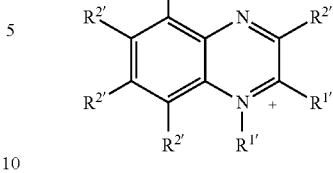
Formula (72)

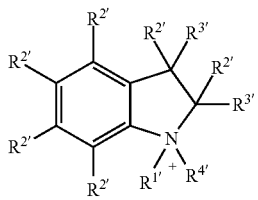
Formula (73)

wherein the substituents $R^{1'}$ to $R^{4'}$ are independently from each other selected from H, CN, linear and branched alkyl rest with 1 to 20 C-atoms, linear or branched alkenyl rest with 2 to 20 C-atoms and one or more non conjugated double bonds, linear or branched alkinyl rest with 2 to 20 C-atoms and one or more non conjugated triple bonds, partly or completely non saturated cycloalkyl rest with 3 to 7 C-atoms which can be substituted with alkyl rests with 1 to 6 C-atoms, saturated and partly or completely non saturated heteroaryls, heteroaryl-$C_1$-$C_6$-alkyl, or alkyl-$C_1$-$C_6$-alkyl, wherein the substituents $R^{1'}$, $R^{2'}$, $R^{3'}$ and/or $R^{4'}$ together can form a ring, wherein one or more of the substituents $R^{1'}$ to $R^{4'}$ can partly or completely be substituted with halogen, particularly with —F and/or —Cl, and —OR', —CN, —C(O)OH, —C(O)NR'$_2$, —SO$_2$NR'$_2$, —C(O)X, —SO$_2$OH, —SO$_2$X, —NO$_2$, wherein the substituents $R^{1'}$ and $R^{4'}$ are not substituted with halogen at the same time, wherein one or two carbon atoms of the substituents $R^{1'}$ and $R^{2'}$, which are non adjacent or bound to an heteroatom, can be substituted by a group selected from —O—, —S—, —S(O)—, —SO$_2$—, —N$^+$R'$_2$—, —C(O)NR'—, —SO$_2$NR'—, and —P(O)R'— wherein R'=H, unsubstituted, partly or completely with —F substituted alkyl with 1 to 6 C-atoms, cycloalkyl with 3 to 7 C-atoms, unsubstituted or substituted phenyl and X=halogen.

Preference is given to $R^{2'}$ selected from —OR', —NR'$_2$, —C(O)OH, —C(O)NR'$_2$, —SO$_2$NR'$_2$)—SO$_2$OH, —SO$_2$X, and —NO$_2$.

Further preferred ionic compounds are disclosed in, e.g., US 2007/0262694 A1.

Further particularly preferred ionic compounds comprise a cation having a structure represented by Formula (74). They include N,N,N-trimethylbutyl ammonium ion, N-ethyl-N,N-dimethyl-propyl ammonium ion, N-ethyl-N,N-dimethylbutyl ammonium ion, N,N,-dimethyl-N-propylbutyl ammonium ion, N-(2-methoxyethyl)-N,N-dimethylethyl ammoniumion, 1-ethyl-3-methyl imidazolium ion, 1-ethyl-2,3-dimethyl imidazoliun ion, 1-ethyl-3,4-dimethyl imidazolium ion, 1-ethyl-2,3,4-trimethyl imidazolium ion, 1-ethyl-2,3,5-trimethyl imidazolium ion, N-methyl-N-propyl pyrrolidinium ion, N-butyl-N-methyl pyrrolidinium ion, N-sec-butyl-N-methylpyrrolidinium ion, N-(2-methoxyethyl)-N-methylpyrrolidinium ion, N-(2-ethoxyethyl)-N-methylpyrrolidinium ion, N-methyl-N-propyl piperidinium ion, N-butyl-N-methyl piperidinium ion, N-sec-butyl-N-methylpiperidinium ion, N-(2-methoxyethyl)-N-methyl piperidiniumion and N-(2-ethoxyethyl)-N-methyl piperidinium ion.

Formula (74)

Very particularly preferred is N-methyl-N-propyl piperidinium.

Particularly preferred ionic compound is a compound selected from the group of ionic compounds, which are soluble in common organic solvents such as toluene, anisole, and chloroform, consisting of methyltrioctylammonium trifluoromethane-sulfonate (MATS), 1-methyl-3-octylimidazolium octylsulfate, 1-butyl-2,3-dimethylimidazolium octylsulfate, 1-octadecyl-3-methylimidazolium bis(trifluoromethylsulfonyl)imide, 1-octadecyl-3-methylimidazolium tris(pentafluoroethyl)trifluorophosphate, 1,1-dipropylpyrrolidimium bis(trifluoromethylsulfonyl)imide, trihexyl(tetradecyl)phosphonium bis(1,2-bezenediolato(2-)-O,O')borate, and N,N,N',N',N',N'-pentamethyl-N'-propylguanidinium trifluoromethanesulfonate.

Further preferred cations are selected from compounds of one of the general Formulae (75) to (80)

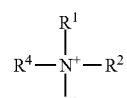

Formula (75)

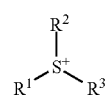

Formula (76)

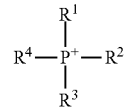

Formula (77)

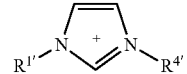

Formula (78)

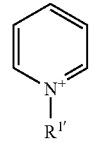

Formula (79)

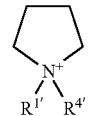

Formula (80)

wherein $R^1$ to $R^4$ are defined as in Formulae (41), (42), and (45), and $R^{1\prime}$ and $R^{4\prime}$ as in Formulae (46), (61), and (56).

Further preferred ionic compound suitable for the fiber device according to the present invention is a compound wherein one of $K^+$ or $A^-$ is covalently bounded to a polymer backbone.

Suitable anions $A^-$ can be selected from $[HSO_4]^-$, $[SO_4]^{2-}$, $[No_3]^-$, $[BF_4]^-$, $[(RF)BF3]^-$, $[(R_F)_2BF_2]^-$, $[(R_F)_3BF]^-$, $[(R_F)_4B]^-$, $[B(CN)_4]^-$, $[PO_4]^-$, $[HPO_4]^{2-}$, $[H_2PO_4]^-$, $[Alkyl-OPO_3]^{2-}$, $[(Alkyl-O)_2PO_2]^-$, $[Alkyl-PO_3]^{2-}$, $[R_FPO_3]^{2-}$, $[(Alkyl)_2PO_2]^-$, $[(R_F)_2PO_2]^-$, $[R_FSO_3]^-$, $[HOSO_2(CF_2)_nSO_2O]^-$, $[OSO_2(CF_2)_nSO_2O]^{2-}$, $[Alkyl-SO_3]^-$, $[HOSO_2(CH_2)_nSO_2O]^-$, $[OSO_2(CH_2)_nSO_2O]^{2-}$, $[Alkyl-OSO_3]^-$, $[Alkyl-C(O)O]^-$, $[HO(O)C(CH_2)_nC(O)O]^-$, $[R_FC(O)O]^-$, $[HO(O)C(CF_2)_nC(O)O]^-$, $[O(O)C(CF_2)_nC(O)O]^{2-}$, $[(R_FSO_2)_2N]^-$, $[(FSO_2)_2N]^-$, $[((R_F)_2P(O))_2N]^-$, $[(R_FSO_2)_3C]^-$, $[(FSO_2)_3C]^-$, $Cl^-$ and/or $Br^-$ wherein:
n=1 to 8;
$R_F$ is fluorinated alkyl of formula $(C_mF_{2m-x+1}H_x)$ with m=1 to 12 and x=0 to 7, wherein for m=1 and x=0 to 2, and/or fluorinated (also perfluorinated) aryl or alkyl-aryl.

The alkyl-group mentioned above can be selected from linear or hyperbranched alkyl groups with 1 to 20 C-atoms, preferably with 1 to 14 C-atoms and particularly preferably with 1 to 4 C-atoms. Preferably $R_F$ means $CF_3$, $C_2F_5$, $C_3F_7$ or $C_4F_9$.

Preferred anions are selected from $PF_6^-$, $[PF_3(C_2F_5)_3]^-$, $[PF_3(CF_3)_3]^-$, $BF_4^-$, $[BF_2(CF_3)_2]^-$, $[BF_2(C_2F_5)_2]^-$, $[BF_3(CF_3)]^-$, $[BF_3(C_2F_5)]^-$, $[B(COOCOO)_2]^-$(BOB), $CF_3SO_3^-$(Tf$^-$), $C_4F_9SO_3^-$(Nf$^-$), $[(CF_3SO_2)_2N]^-$(TFSI$^-$), $[(C_2F_5SO_2)_2N]^-$(BETI), $[(CF_3SO_2)(C_4F_9SO_2)N]^-$, $[(CN)_2N]^-$(DCA$^-$), $[CF_3SO_2]_3C]^-$, and $[(CN)_3C]^-$.

Preferably, the said EL-F comprises further in EML a ion conducting material, which can have a concentration of 1 to 50 wt %, preferably 2 to 40 wt %, particularly preferably 3 to 20 wt %, and very particularly preferably 5 to 15 wt % with respect to the total amount of the layer.

The suitable ion conductors can be selected from polymeric materials, such as perfluorosulfonic acid-based formulations, polybenzimidazoles, sulfonated polyetherketone, sulfonated naphthalenic polyimides, and polyethylene oxide (PEO)-based formulations. A preferred ion conductor for Li$^+$ is polyethylene oxide (PEO) or derivatives.

Typically a EL-F comprising ionic specie has the following layer structure fiber core:
1) Fiber core;
2) First electrode
3) Optionally a buffer layer
4) EML, which comprise at least one quantum dot and at least one ionic specie;
5) Optionally a buffer layer
6) Second electrode, which is at least partially transparent to the emission from the EML.

The typical buffer layer between anode and the EML an be selected from polymeric hole injection layer, which is used for OLED, for example PEDOT:PSS.

Preferably the EL-F is characterized in that the at least one quantum dot, which is electrically neutral, and at least one organic functional material selected from host materials, fluorescent emitters, phosphorescent emitters, HTMs, HIMs, ETMs, EIMs, hole blocking materials (HBMs), and electron blocking materials (EBMs), which is either electrically neutral or ionic and optionally the at least one ionic species are located in the EML of the fiber.

The fiber according to one or more of claims 1 to 10, characterized in that the device is a quantum-dot light emitting diode (QD-LED).

The suitable comprising, in the sequence as described below
optionally a first substrate,
an anode layer,
optionally a hole injection layer,
optionally a hole transport layer,
an emissive layer comprising at least one nanocrystal, as described above and below, optionally an electron transport layer,
optionally an electron injection layer,
a cathode layer, which is at least partially transparent to the emission from the EML.
optionally a second substrate.
wherein either the first substrate or the second substrate is a fiber substrate.

In another preferred embodiment the EL-F comprises at least one quantum dot and at least one further organic functional material selected from host materials and emissive materials, preferably emissive metal complexes in the EML, characterized in that the emission wavelength(s) of the emissive metal complexe(s) is (are) shorter as compared to the emission wavelength(s) of the quantum dot(s).

More preferably, the emission spectrum of the emissive metal complex overlaps with the absorption spectrum of the nanocrytsal, which enables the Förster-Transfer from metal complex to nanocrytsal. The advantage of this embodiment is one may make efficient nanocrytsal emissive device with narrow spectrum from an efficient phosphorescent OLED.

In yet another preferred embodiment the EL-F comprises at least one quantum dot and at least one further organic functional material selected from host materials and emissive materials, preferably emissive metal complexes in the EML, characterized in that the emission wavelength(s) of the emissive metal complexe(s) is (are) shorter as compared to the emission wavelength(s) of the quantum dot(s).

The present invention also relates to a method for the preparation of EL-F comprising QDs. The method for the preparation comprises the following steps:

The EL-F according the present invention can be typically prepared as follows:
a. Clean the fiber core
  The cleaning process which is typically used for glass fibers can also be used for fiber cores of EL-F: fiber cores are degreased with solvents and then cleaned by exposure to a UV-ozone ambient. The specific cleaning process can be adopted according to the specific fiber core used.
b. Deposition the first electrode, by conformally evaporating metal or coating from a solution or formulation comprising a conducitive material. When employing the conformal evaporation, the fiber is axially rotated at a desired speed during the evaporation, for example from 30-60 rpm, to achieve uniformity. This is a preferred method when metal anodes are used.
  In another preferred embodiment, the anode can be coated from an ink or solution or a formulation comprising a conductive material. Such conductive material can be metal or metal oxide nanoparticle, which can be dissolved in the solution or dispersed in the formulation, for example Ag or ITO, and organic conductive materials, for example PEDOT:PSSH. Suitable coating methods can be selected from dip coating, spin coating, ink jet printing, letter-press printing, screen printing, doctor blade coating, roller printing, reverse-roller printing, offset lithography printing, flexographic printing, web printing, spray coating, brush coating or pad printing, and slot-die coating, preferably from dip-coating or spray coating; The said formulation can be a solution, a dispersion, or an emulsion comprising one continuous phase and a discontinuous phase (nanodroplet). The electrode is heated to remove residual solvent(s).
  A further suitable method for the deposition of electrode is the electrochemical deposition, for example galvanic deposition of metals, e.g. aluminium, which represents a potential low-cost method for mass production.
c. Deposition of the EML by coating a solution or formulation comprising at least one nanocrystal and/or at least one organic functional compound and/or at least one ionic compound. Suitable coating methods can be selected from dip coating, spin coating, ink jet printing, letter-press printing, screen printing, doctor blade coating, roller printing, reverse-roller printing, offset lithography printing, flexographic printing, web printing, spray coating, brush coating or pad printing, slot-die coating, particularly preferably by dip-coating or spray coating. The said formulation can be a solution, a dispersion, or an emulsion comprising one continuous phase and a discontinuous phase. If the ionic compound and the organic emissive compound are not soluble in a common solvent, the emulsion or dispersion is preferred. The examples of such dispersion and emulsion can be referred to WO 2003/050147, EP 09015860.1, EP 09015861.9, and EP 09015862.7.
d. Deposition the second electrode; The same method as described for the first electrode can be applied for the second electrode.
e. Optionally, encapsulation of the fiber device.

If further additional functional layers, for example HTL, HIL, ETL, EIL, EBL and HBL, exists, they can be deposited either by conformal evaporation as described in b, or from solution as described in c.

Encapsulation can be achieved by using a UV-cured resin, for example epoxy resin, or a thin film comprising for example $SiN_x$, $SiO_x$, $Al_2O_3$ etc. The OLEFCs according to the present invention can be preferably mass produced using dip-coating. One general production line is schematically shown in FIG. 3, taking, for example, an OLEFC having a structure of anode/HIM/interlayer/EML/cathode, wherein the electrodes are deposited by physical vapor deposition and the organic function layers, HIM, interlayer and EML are coated by dip-coating. The physical vapor deposition methods could be selected from such as thermal vacuum evaporation, sputtering, Cathodic Arc Deposition, Pulsed laser deposition and e-beam etc. Another particularly preferred production method is all solution based, as schematically shown in FIG. 4. The components used in both FIGS. 3 and 4 are explained as follows: 210 is a fiber core; 130 is a deposition chamber for the first electrode; 200 is a deposition chamber for the second electrode; 240 is a container comprising an ink comprising a conductive material for the first electrode; 140 is a container containing solution of buffer material or HIM; 160 is a container containing a solution or a formulation of HTM or interlayer material; 180 is a container containing a solution or a formulation of an emissive composition; 250 is a container containing an ink comprising a conductive material for the second electrode; 150, 170, 190, 220 and 230 are dryers.

The devices prepared according to this method have advantages over OLED device and flat QD-LED in that: 1) compared to OLED, nanocrystal fiber EL devices have narrower emission band, thus gaining potential to get purer color and high efficiency: 2) compared to flat QD-LED, the most suitable method to prepare QD-LED is drop-casting (in mass-production) or spin-cast (in lab); in drop casting, both sides of the flat substrate will be coated, therefore another step is needed to remove the coating on the unwanted side. This problem can be removed in fiber device according the present invention; 3) further, for an electronic device based on nanorods, the prerequisite is to get well-ordered nanorod films. So for, several methods are developed by means of external perturbations, such as, for example, external electric fields, as reported by Harnack et al., Nano Lett. 2003, 3 (8), 1097-1101, by the Langmuir-Blodgett technique, as reported by Kim et al., J. Am. Chem. Soc. 2001, 123 (18), 4360-4361, or by exploiting the interfacial tension between two immiscible liquid phases, as reported by Wang et al., J. Colloid Interface Sci. 2008, 318, 82-87. Nevertheless, despite the tremendous efforts devoted up to now, the ability to produce ordered and large scale assemblies of nanorods needs further advancements for their technological potential to be truly exploited in electronic devices. To date, efforts in this direction have remained confined to an isolated example of fabrication of LEDs emitting some degree of polarized light from layers of CdSe/CdS core/shell quantum rods aligned either in a stretched polymer matrix or by rubbing, as reported by Hikmet et al., Adv. Mater. 2005, 17 (11), 1436-1439. According the method of the present invention, the nanorods can be arranged along the fiber axis during the drop-coating, having a very specific and new structure, therefore providing a simple way to produce polarised light emitting device.

Furthermore, the present invention relates to a EL-F comprising at least one nanocrystal obtainable by a method described above. The structure of the resulting fiber is specific to the method of preparation and shows the above mentioned technical effects.

The EL-F and/or devices according to the present invention can be used to treat medical and/or cosmetic conditions. Thus, another subject of the present invention is the use of said EL-F and/or devices comprising them for the treatment and/or prophylaxis and/or diagnosis of diseases and/or cosmetic conditions.

Hereby any therapeutic strategy is included, i.e. treatment of a subject with light can be performed with or without a combination with other treatment approaches. Treatment can, for example, be carried out with one or more wavelengths in one or more devices comprising the EL-F(s) of the present invention. Furthermore, in addition to devices comprising said EL-Fs, further light sources using different technologies can be used for the treatment, such as LEDs (light emitting diodes) and lasers. In addition, the treatment with said EL-F(s) and/or devices comprising them can be combined with any known treatment strategy using drugs and cosmetics.

If phototherapy is combined with the treatment of chemical compounds such as a drugs and/or cosmetics light can be used to initiate a (photo-) chemical reaction or activation of the chemical compounds, which is called photodynamic therapy (PDT). Phototherapy according to the present invention can also be used in conjunction with chemical compounds without initiating a photochemical reaction or activation. Synergistic effects for the effectiveness and safety of the treatment of a therapeutic disease can arise from sequential, parallel, and overlapping treatment with both light therapy and drugs and/or cosmetics. The drug(s) or cosmetic compound(s), e.g., can be administered first for a specific time period followed by the application of phototherapy using the EL-Fs according to the present invention or devices comprising them. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is, at least in part, due to the fact, that smaller doses of the drugs may be required when following the combined approach as outlined herein.

Many diagnostic devices comprise light sources for either illumination only or as functional component for the diagnosis itself, e.g. for the determination of blood parameters such as oxygen. Thus the present invention also relates to said EL-Fs for diagnostic purposes. The use of light sources comprising the said EL-Fs for diagnostic purposes is also subject of the present invention. Based on the teaching of the present invention, one skilled in the art will have no problems to develop diagnostic devices for which light sources are required comprising the said EL-Fs.

Treatment is any exposure of a subject to the radiation of said EL-Fs. The treatment may be performed by direct contact between the subject and the device comprising the EL-Fs or without direct contact between them. The treatment may be outside or inside the subject. Treatment outside the subject may be, for instance, treatment of the skin, wounds, eye, gingival, mucosa, tongue, hair, nail bed, and nails. Treatment inside the subject may be, for instance, treatment of blood vessels, heart, breast, lung, or any other organ of the subject. Particular devices are required for most applications inside the subject. One such example may be a stent comprising one or more EL-Fs according to the present invention. Said subject to be treated may preferably be a human or an animal. The term cosmetic also includes aesthetic applications.

The wavelength of light that is emitted by the EL-Fs and/or devices when incorporated in any kind of electronic device can be precisely tailored by the selection of the appropriate components of the EL-Fs. This includes, as outlined above, the specific design of the quantum dots and the use of different emitters or colour filter and colour converter. Depending on the application of the EL-Fs each therapeutic or cosmetic treatment requires a more or less defined wavelength or spectrum of wavelengths to be emitted.

As outlined above one effect of phototherapy is the stimulation of metabolism in the mitochondria. After phototherapy, the cells show an increased metabolism, they communicate better and they survive stressful conditions in a better way.

Said EL-F(s) and/or the said devices comprising them can be used for cellular stimulation. Preferred wavelengths or ranges of wavelengths for cellular stimulation are in the range between 600 to 900 nm, particularly preferable between 620 and 880 nm, and very particularly preferably between 650 and 870 nm. Examples of particularly preferred wavelengths for cellular stimulation are 683.7, 667.5, 772.3, 750.7, 846, and 812.5 nm.

Any therapeutic disease and/or cosmetic condition approachable by phototherapy can be treated with EL-Fs according to the present invention and said devices. These diseases and/or conditions include, e.g., skin diseases, and skin-related conditions including skin-ageing, and cellulite, enlarged pores, oily skin, folliculitis, precancerous solar keratosis, skin lesion, aging, wrinkled and sun-damaged skin, crow's feet, skin ulcers (diabetic, pressure, venous stasis), acne rosacea lesions, cellulite; photomodulation of sebaceous oil glands and the surrounding tissues; reducing wrinkles, acne scars and acne bacteria, inflammation, pain, wounds, psychological and neurological related diseases and conditions, edema, Pagets disease, primary and metastatic tumors, connective tissue disease, manipulation of collagen, fibroblast, and fibroblast derived cell levels in mammalian tissue, illuminating retina, neoplastic, neovascular and hypertrophic diseases, inflammation and allergic reactions, perspiration, sweating and hyperhydrosis from eccrine (sweat) or apocrine glands, jaundice, vitiligo, ocular neovascular diseases, bulimia nervosa, herpes, seasonal affective disorders, mood, sleep disorders, skin cancer, crigler naijar, atopic dermatitis, diabetic skin ulcers, pressure ulcers, bladder infections, relief of muscular pains, pain, stiffness of joints, reduction of bacteria, gingivitis, whitening teeth, treatment of teeth and tissue in mouth, wound healing.

Cosmetic conditions are preferably selected from acne, skin rejuvenation and skin wrinkles, cellulite, and vitiligo.

Preferably the said EL-Fs are used for the treatment and/or prophylaxis of humans and/or animals. Particularly preferably the EL-Fs according to the present invention are used for the treatment and/or prophylaxis of humans.

Further subjects suitable to be treated by the irradiation with EL-Fs and/or devices according to the present invention are plants, microbes, bacteria, fungi, and liquids. Microbes include, but are not limited to, prokaryotes such as bacteria and archaea and eukaryotes such as protists, animals, fungi and plants. Preferred liquids are beverages and particularly preferably water.

Preference is given to the use of EL-Fs and/or devices comprising them for the treatment and/or prophylaxis and/or diagnosis of skin diseases and/or cosmetic skin conditions.

Skin as used herein is defined as the largest organ of the integumentary system including hair, scales, feathers and nails. The term skin, as defined herein, also includes the tongue, mucosa and gingival.

As already mentioned, principally any therapeutic and cosmetic condition that is approachable by phototherapy is covered by the present invention.

The skin diseases and skin related conditions include, but are not limited to acneiform eruptions, autoinflammatory skin diseases or conditions, chronic blistering, conditions of the mucous membranes, conditions of the skin appendages, conditions of the subcutaneous fat, connective tissue diseases, abnormalities of dermal fibrous and elastic tissue, dermal and subcutaneous growths, dermatitis, atopic dermatitis, contact dermatitis, eczema, pustular dermatitis, seborrheic dermatitis and eczema, disturbances of pigmentation, drug eruptions, endocrine-related diseases and conditions, epidermal nevi diseases and conditions, neoplasms, cysts, erythemas, genodermatoses, infection-related diseases and conditions, bacterium-related diseases and conditions, mycobacterium-related diseases and conditions, mycosis-related diseases and conditions, parasitic infestations, stings, and bites, virus-related diseases and conditions, lichenoid eruptions, lymphoid-related diseases and conditions, melanocytic nevi and neoplasms, monocyte- and macrophage-related diseases and conditions, mucinoses, neurocutaneous, noninfectious immunodeficiency-related diseases and conditions, nutrition-related diseases and conditions, papulosquamous hyperkeratotic related diseases and conditions, pruritic related diseases and conditions, psoriasis (mild, mild to severe, and severe), reactive neutrophilic diseases and conditions, recalcitrant palmoplantar eruptions, diseases and conditions resulting from errors in metabolism, diseases and conditions resulting from physical factors, urticaria and angioedema, vascular-related diseases and conditions, and periodontitis or other diseases and conditions of the gingival.

Skin related diseases and conditions also include skin tumors, pre-malignant tumors, malignant tumors, cell carcinomas, secondary metastasis, radiodermatitis and keratosis.

The healing of wounds can also be assigned to skin diseases and skin related conditions. Wound healing can, hereby, occur at the outer surface of the subject to be treated, at its internal parts, at the skin, eye, nail or nail bed, any surface in the subject's mouth, and at the mucosa, gingival, epithelial surface of the vascular system or other part of the subjects body.

Preference is given to the treatment and/or prophylaxis and/or diagnosis of skin diseases and/or cosmetic skin conditions selected from acne, psoriasis, eczema, dermatitis, atopic dermatitis, atopic eczema, edema, vitiligo, skin ageing, skin, wrinkles, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, skin redness, comedo, and cellulite.

The EL-Fs and devices according to the present invention can be used in cosmetics for skin care and skin repair, e.g. as light plaster. The wavelengths or range of wavelengths emitted by said EL-Fs and/or devices is in the range between 400 and 800 nm, preferably between 450 and 750 nm, particularly preferably between 500 and 700 nm, and very particularly preferably between 580 and 640 nm.

Preferred skin diseases and skin-related conditions are selected from acne, psoriasis, eczema, edema, dermatitis, atopic dermatitis, vitiligo, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, and cellulite Further preferred skin diseases and skin-related conditions are selected from psoriasis, polymorphous light eruption, solar urticaria, actinic reticuloid atopic eczema, vitiligo, pruritus, lichen planus, early cutaneous T-cell lymphoma, dermographism, and pityriasis lichenoides. Preferably theses diseases and conditions are treated with light having a wavelength or a range of wavelengths between 200 and 500 nm, particularly preferably between 250 and 400 nm, and very particularly preferably between 270 and 350 nm.

Said EL-Fs and/or devices can be used for PUVA therapy. PUVA therapy is derived from the therapeutic application of psoralen (7H-furo[3,2-g]chromen-7-one) and derivatives thereof together with UV-A light. PUVA can be employed for the treatment of skin diseases characterized by hyperproliferative conditions. Psoralen is the parent compound in a family of natural products. It is structurally related to coumarines and can preferably be used for the treatment of psoriasis, eczema, vitiligo, mycosis fungoides, cuntaneous T-cell lymphoma, and other autoimmune diseases. With PUVA can also bet treated atopic eczema, lichen planus, urticaria pigmentosa, polymorphous light eruption, and alopecia areata.

Psoralen can be administered orally or topically to the skin. Preferred compounds are psoralen, 8-methoxypsoralen (8-MOP), 5-methoxypsoralen (5-MOP), and 4,5',8-trimethylpsoralen (TMP). After oral administration of 8-MOP, patients become gradually reactive to UV-A and therefore to photochemotherapeutic treatment. The patients are maximally reactive 2 to 3 hours after ingestion of the drug, and during this period the irradiation is carried out.

In the case of vitiligo khellin can be used instead of psoralen. The combined treatment with light and khellin is often called KUVA.

The EL-F(s) and/or devices of the present invention can also be used for photopheresis. Photphoreresis is a process by which peripheral blood is exposed in an extracorporeal flow system to photoactivate 5-MOP and represents a treatment for disorders caused by aberrant T lymphocytes. It is a therapy for advanced cutaneous T-cell lymphoma, pemphigus vulgaris and progressive systemic sclerosis (scleroderma). It can be used to treat autoimmune disorders. Further diseases that can be treated include multiple sclerosis, organ transplant rejection, rheumatoid arthritis, and AIDS.

The present invention particularly refers to EL-Fs and or devices according to the present invention for the treatment of acneiform eruptions. The term acneiform eruption refers to a group of dermatoses including acne vulgaris, rosacea, folliculitis, and perioral dermatitis. Acneiform eruptions are, generally spoken, caused by changes in the pilosebaceous unit and are selected from acne aestivalis (Mallorca acne), acne conglobata, acne cosmetica, acne fulminans (acute febrile ulcerative acne), acne keloidalis (acne keloidalis nuchae, dermatitis papillaris capillitii, folliculitis keloidalis, folliculitis keloidis nuchae, nuchal keloid acne), acne mecánica, acne medicamentosa, acne miliaris necrotica (acne varioliformis), acne vulgaris, acne with facial edema (solid facial edema), acneiform eruptions, blepharophyma, erythrotelangiectatic rosacea (erthemaotelangiectatic rosacea), excoriated acne (acne excoriée des jeunes filles, Picker's acne), glandular rosacea, gnathophyma, gram-negative rosacea, granulomatous facial dermatitis, granulomatous perioral dermatitis, halogen acne, hidradenitis suppurativa (acne inversa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum), occupational acne, ophthalmic rosacea (ocular rosacea, ophthalmorosacea), otophyma, persistent edema of rosacea (chronic upper facial erythematous edema, Morbihan's disease, Rosaceous lymphedema), pomade acne, papulopustular rosacea, perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobata, rosacea fulminans, SAPHO syndrome, steroid rosacea, tropical acne.

Acne vulgaris (commonly called acne) is a common skin condition, caused by changes in pilosebaceous units, skin structures consisting of a hair follicle and its associated sebaceous gland, via androgen stimulation. It is characterized by noninflammatory follicular papules or comedones and by inflammatory papules, pustules, and nodules in its more severe forms. Acne vulgaris affects the areas of skin with the densest population of sebaceous follicles; these areas include the face, the upper part of the chest, and the back. Severe acne is inflammatory, but acne can also manifest in noninflammatory forms. Acne lesions are commonly referred to as pimples, blemishes, spots, zits, or simply acne.

Acne occurs most commonly during adolescence, affecting more than 89% of teenagers, and frequently continues into adulthood. In adolescence, acne is usually caused by an increase in male sex hormones, which people of both genders accrue during puberty. For most people, acne diminishes over time and tends to disappear—or at the very least decrease—after one reaches one's early twenties. There is, however, no way to predict how long it will take to disappear entirely, and some individuals will carry this condition well into their thirties, forties and beyond.

The face and upper neck are the most commonly affected, but the chest, back and shoulders may have acne as well. The upper arms can also have acne, but lesions found there are often keratosis pilaris. Typical acne lesions are comedones, inflammatory papules, pustules and nodules. Some of the large nodules are also called cysts and the term nodulocystic has been used to describe severe cases of inflammatory acne.

Aside from scarring, its main effects are psychological, such as reduced self-esteem and, in some cases, depression or suicide. Acne usually appears during adolescence, when people already tend to be most socially insecure. Early and aggressive treatment is therefore advocated by some to lessen the overall impact to individuals.

Light exposure can be used as treatment for acne. Used twice weekly, this has been shown to reduce the number of acne lesions by about 64% and is even more effective when applied daily. The mechanism appears to be that a porphyrin (Coproporphyrin III) produced within *P. acnes* generates free radicals when irradiated by 420 nm and shorter wavelengths of light. Particularly when applied over several days, these free radicals ultimately kill the bacteria. Since porphyrins are not otherwise present in skin, and no UV light is employed, it appears to be safe.

The treatment apparently works even better if used with a mixture of the violet/blue light and red visible light (e.g. 660 nm) resulting in a 76% reduction of lesions after three months of daily treatment for 80% of the patients; and overall clearance was similar or better than benzoyl peroxide. Unlike most of the other treatments few if any negative side effects are typically experienced, and the development of bacterial resistance to the treatment seems very unlikely. After treatment, clearance can be longer lived than is typical with topical or oral antibiotic treatments; several months is not uncommon. In addition, basic science and clinical work by dermatologists has produced evidence that intense blue/violet light (405 to 425 nm) can decrease the number of inflammatory acne lesion by 60 to 70% in four weeks of therapy, particularly when the *P. acnes* is pre-treated with delta-aminolevulinic acid (ALA), which increases the production of porphyrins.

The present invention therefore also relates to a combination of the said EL-Fs or said devices and active drugs or active ingredients for the treatment of therapeutic diseases and/or cosmetic conditions. In particular, the present invention relates to the combined use of said EL-Fs and drugs used for the treatment of acne. The drugs can be selected from any drugs typically employed in order to treat acne, such as antibiotics (topical and/or oral), hormonal treatments, topical retinoids, topical bactericidals, sulfur. Suitable topical bactericidals are, for example, benzoyl peroxide, triclosan, and chlorhexidine gluconate. Suitable topical antibiotics are, for example, erythromycin, clindamycin, and tetracycline. Suitable oral antibiotics are, for example, erythromycin, tetracycline antibiotics (e.g. oxytetracycline, doxycycline, minocycline, or lymecycline), trimethoprim, and minocycline.

Suitable hormones are, e.g., selected from estrogen, progestogen, a combination of estrogen and progestogen, cyproterone, oestrogen, a combination of cyproterone and oestrogen, drospirenone, spironolactone, and cortisone. Suitable oral retinoids are, for example, vitamin A derivatives such as isotretinoin (e.g. Accutane, Amnesteem, Sotret, Claravis, Clarus). Suitable topical retinoids are, for example, tretinoin (e.g. Retin-A), adapalene (e.g. Differin), tazarotene (e.g. Tazorac), isotretinoin, and retinol. Further suitable drugs are, e.g. selected from anti-inflammatory drugs.

The EL-Fs according to the present invention and devices comprising them can also be used in combination with dermabrasion to treat or prevent acne. Dermabrasion is a cosmetic medicinal procedure in which the surface of the skin is removed by abrasion (sanding).

Hereby any therapeutic strategy is included. The drug, e.g., can be administered first for a specific time period followed by the application of phototherapy using the EL-Fs or said devices according to the present invention. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is due to the fact, that smaller doses of the drugs may be required when following the combined approach as outlined herein.

Comedones, also called blackhead, can also be treated by phototherapy employing the EL-Fs or devices according to the present invention. A comedon is a yellow or blackish bump or plug on the skin. Actually, it is a type of acne vulgaris. Comedones are caused by excess oils that have accumulated in the sebaceous gland's duct. The substance found in these bumps mostly consists of keratin and modified sebum, which darkens as it oxidizes. Clogged hair follicles, where blackheads often occur, reflect light irregularly to produce a comedon. For this reason, the blockage might not necessarily look black when extracted from the pore, but may have a more yellow-brown colour as a result of its melanin content.

In contrast, a so called whitehead, which is also called closed comedo, is a follicle that is filled with the same material, sebum, but has a microscopic opening to the skin surface. Since the air cannot reach the follicle, the material is not oxidized, and remains white.

The EL-Fs or devices according to the present invention used for the treatment of acne preferably comprises at least one organic electroluminescent compound which emits light in the range between 350 and 900 nm, preferably between 380 and 850 nm, particularly preferably between 400 and 850 nm, and very particularly preferably between 400 and 800 nm.

Further particularly preferred light for the treatment of acne is blue light. Preferred blue light has emission wavelengths for the treatment of acne are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430 nm. For example 414 and 415 nm are particularly suitable in order to kill P. acnes bacteria and to help cure existing blemishes and to prevent further outbreaks.

Studies on the application of phototherapy to treat acne revealed that a combination of different wavelengths or ranges of wavelengths are particularly suitable to treat acne efficiently. Particularly preferred is therefore a combination of red light and blue light to treat acne. The said red light is preferably selected from the range between 590 to 750 nm, particularly preferably between 600 and 720 nm, and very particularly preferably between 620 and 700 nm. Two further preferred wavelengths for the treatment of acne are 633 and 660 nm. The blue light can be selected from the wavelengths as described above.

In the case of comedo EL-Fs comprising light emitting compound(s) emitting light with a wavelength of 500 nm or light in the range between 500 and 700 nm are particularly preferred.

Cellulite describes a condition that is claimed to occur in most women, where the skin of the lower limbs, abdomen, and pelvic region becomes dimpled. The causes of cellulite are poorly understood and may involve changes in metabolism and physiology such as gender specific dimorphic skin architecture, alteration of connective tissue structure, vascular changes and inflammatory processes. A couple of therapies are applied to prevent or to treat cellulite. Heat and the increase of blood flow are two common techniques. Therefore light therapy is considered to be beneficial to individuals suffering from cellulite. EL-Fs and/or devices according to the present invention are suitable for the treatment and/or prophylaxis of cellulite. PDT is also suitable for the treatment and/or prophylaxis of cellulite.

The wavelength for the treatment and/or prophylaxis of cellulite that is to be emitted by the EL-Fs and/or devices according to the present invention is in the range between 400 and 1000 nm, preferably in the range between 400 and 900 nm, particularly preferably between 450 and 900 nm, and very particularly preferably between 500 and 850 nm.

The more general term skin ageing refers to both the formation of wrinkles and hyperpigmentation. The signs of ageing of the human skin resulting from the effects on the skin of intrinsic and extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telnagiectasia.

Some of these signs are more particularly associated with intrinsic or physiological ageing, that is so to say with "normal" ageing associated with age, whereas others are more specific to extrinsic ageing, that is so to say ageing caused by the environment in general; such ageing is more particularly photo-ageing due to exposure to the sun. Other factors causing ageing of the skin are atmospheric pollution, wounds, infections, traumatisms, anoxia, cigarette smoke, hormonal status, neuropeptides, electromagnetic fields, gravity, lifestyle (e.g. excessive consumption of alcohol), repetitive facial expressions, sleeping positions, and psychological stressors.

The changes in the skin which occur due to intrinsic ageing are the consequence of a genetically programmed sequence involving endogenous factors. This intrinsic ageing in particular causes slowing down of the regeneration of skin cells, which is reflected essentially in the appearance of clinical damage such as a reduction of the subcutaneous adipose tissue and the appearance of fine lines or small wrinkles, and in histopathological changes such as an increase in the number and thickness of the elastic fibers, a loss of vertical fibers from the elastic tissue membrane and the presence of large irregular fibroblasts in the cells of this elastic tissue.

In contrast, extrinsic ageing results in clinical damage such as thick wrinkles and the formation of flabby and weather-beaten skin, and in histopathological changes such as an excessive accumulation of elastic substance in the upper dermis and degeneration of the collagen fibers.

There are different biological and molecular mechanisms which are responsible for he ageing of the skin and the process is currently not fully understood. However, it was recognized that both ilntrinsic and extrinsic factors of ageing of the skin share common mechanisms [P. U. Giacomoni et al., Biogerontology 2004, 2, 219-229]. These factors trigger a process leading to the accumulation of damages in the skin resulting in skin ageing since the expression of cell adhesion molecules provokes recruitment and diapedesis of circulating immune cells, which digest the extracellular matrix (ECM) by secreting collagenases, myeloperoxidases and reactive oxygen species.

The activation of these lytic processes provokes random damage of these resident cells, which in turn secrete prostaglandins and leukotrienes. These signaling molecules induce the degranulation of resident mast cells which release the autacoid histamine and the cytokine TNFalpha thus activating endothelial cells lining adjacent capillaries which release P-selectin and the synthesis of cell adhesion molecules such as E-selectin and ICAM-1. This closes a self-maintained micro-inflammatory cycle, which results in the accumulation of ECM damage, i.e. skin ageing.

There is a strong cosmetic and therapeutic need for novel strategies for the treatment or prophylaxis of skin ageing. Various cosmetic and therapeutic compositions (including for skin care) intended inter alia to prevent or treat ageing of the skin are known. Retinoic acid and derivatives thereof have been described as anti-ageing agents in skin care, cosmetic, or dermatological compositions, in particular in U.S. Pat. No. 4,603,146. Hydroxy acids such as lactic acid, glycolic or alternatively citric acid are also known for this same application, these acids have been described in numerous patents and publications (e.g. EP-A-413528) and introduced into numerous skin care, cosmetic, or dermatological compositions on the market. Aromatic orthohydroxy acids such as salicylic acid have also been proposed (e.g. WO 93/10756 and WO 93/10755).

All of these compounds act against ageing of the skin by desquamation, that is to say removal of the dead cells at the surface of the stratum corneum. This desquamation is also referred to as a keratolytic property. However, these compounds also have side effects, consisting of stinging and redness, which the user finds unpleasant. Thus, there remains a need for anti-ageing methods which are at least as effective as the known compounds, but do not exhibit their drawbacks. Unlike the established strategies to treat or prevent skin ageing, modulating the selectin function is a novel concept intervening the micro-inflammation cascade at a very early stage and treating and preventing intrinsic and extrinsic skin ageing according to the present inventions represents a strategy without the drawbacks known from other strategies.

Phototherapy provides a new way to treat ageing of the skin. Thus, another subject of the invention is the use of the EL-Fs and/or devices according to the present invention for the treatment and/or prophylaxis of skin ageing. This means, that the present invention provides solutions, inter alia, for skin rejuvenation and to reduce or prevent the formation of wrinkles.

The wavelength for the treatment of skin ageing that is to be emitted by the EL-Fs and/or devices according to the present invention is in the range between 400 and 950 nm. Preferably the wavelength is in the range between 550 and 900 nm, and particularly preferably between 550 and 860 nm.

The EL-Fs and/or devices of the present invention may also emit light of different wavelengths or wavelength ranges which also applies for other embodiments of the present invention.

In another preferred embodiment of the present invention the EL-Fs and/or devices used for the treatment of skin ageing emits light in the range of 600 nm and 650 nm, particularly preferably in the range between 620 nm and 650 nm.

The EL-Fs and/or devices according to the present invention used for the treatment and/or prevention of skin ageing preferably comprises at least one organic electroluminescent compound which emits light in the range between 350 and 950 nm, preferably between 380 and 900 nm, and particularly preferably between 400 and 900 nm.

Further particularly preferred light for the treatment and/or prophylaxis of skin ageing is blue light. Preferred blue light has emission wavelengths for the treatment and/or prophylaxis of skin ageing are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, and 430 nm. For example 415 nm is particularly suitable.

Further particular preferred light for the treatment and/or prophylaxis of skin ageing has a wavelength between 400 and 900 nm.

Skin rejuvenation can also be achieved with light of the wavelength of 830 nm or slightly below or above that value. Therefore, EL-Fs and/or devices according to the present invention emitting light in the range between 700 nm and 1000 nm, preferably between 750 nm and 900 nm, particularly preferably between 750 nm and 860 nm, and very particularly preferably between 800 nm and 850 nm are also subject of the present invention.

Redness of the skin of a subject can be treated by a EL-Fs and/or devices according to the present invention. The wavelength for the treatment and/or prophylaxis of redness that is to be emitted by the EL-Fs and/or devices according to the present invention is in the range between 460 and 660 nm. Preferably the wavelength is in the range between 500 and 620 nm, and particularly preferably between 540 and 580 nm. One particular preferred wavelength for this purpose is 560 nm.

Dermatitis of a subject can be treated by a EL-Fs and/or devices according to the present invention. The wavelength for the treatment and/or prophylaxis of dermatitis that is to be emitted by the EL-Fs and/or devices according to the present invention is in the range between 470 and 670 nm. Preferably the wavelength is in the range between 490 and 650 nm, and particularly preferably between 530 and 610 nm. Two particular preferred wavelengths for this purpose are 550 nm and 590 nm.

Atopic eczema of a subject can be treated by a EL-Fs and/or devices according to the present invention. The wavelength for the treatment and/or prophylaxis of atopic eczema that is to be emitted by the EL-Fs and/or devices according to the present invention is in the range between 470 and 670 nm. Preferably the wavelength is in the range between 490 and 650 nm, and particularly preferably between 530 and 610 nm. One particular preferred wavelength for this purpose is 320 nm.

Psoriasis can be treated by a EL-Fs and/or devices according to the present invention. The wavelength for the treatment and/or prophylaxis of psoriasis that is to be emitted by the EL-Fs and/or devices according to the present invention is in the range between 240 and 500 nm. Preferably the wavelength is in the range between 290 and 400 nm, and particularly preferably between 300 and 330 nm. Two particular preferred wavelengths for this purpose are 311 and 320 nm.

Vitiligo can be treated by a EL-Fs and/or devices according to the present invention. The wavelength for the treatment and/or prophylaxis of vitiligo that is to be emitted by the EL-Fs and/or devices according to the present invention is in the range between 240 and 500 nm. Preferably the wavelength is in the range between 290 and 400 nm, and particularly preferably between 300 and 330 nm. One particular preferred wavelength for this purpose is 311 nm.

Targeted phototherapy has enabled therapeutic dosing of ultraviolet light to specific dermatoses while minimizing exposure of healthy skin. Specifically, the 308 nm wavelength of light within the ultraviolet B range has been shown as particularly effective for many dermatoses, including vitiligo; psoriasis; and leukoderma such as that associated with scars, striae alba and post-$CO_2$ laser resurfacing.

The EL-Fs and/or devices of the present invention can also be used for the treatment of edema. Edema, formerly known as dropsy or hydropsy, is an abnormal accumulation of fluid beneath the skin or in one or more cavities of the body. Generally, the amount of interstitial fluid is determined by the balance of fluid homeostasis, and increased secretion of fluid into the interstitium or impaired removal of this fluid may cause edema. Five factors can contribute to the formation of edema: (1) It may be facilitated by increased hydrostatic pressure or by reduced oncotic pressure within blood vessels or (2) by increased blood vessel wall permeability as in inflammation or (4) by obstruction of fluid clearance via the lymphatic or (5) by changes in the water retaining properties of the tissues themselves. Raised hydrostatic pressure often reflects retention of water and sodium by the kidney.

The EL-Fs and/or devices according to the present invention used for the treatment of edema preferably emit light in the range between 760 and 940 nm, preferably between 780 and 920 nm, particularly preferably between 800 and 900 nm, and very particularly preferably between 820 and 880 nm.

One further particularly preferred emission wavelength for the treatment of edema is 850 nm.

Another subject of the present invention relates to EL-F(s) and/or devices according to the present invention for the treatment and/or prophylaxis of infections and inflammatory, neurological, and psychological diseases and/or conditions.

Many inflammatory diseases, disorder, and conditions can be treated with phototherapy. EL-Fs and/or devices according to the present invention for the treatment and/or prophylaxis of inflammatory disorders is also subject of the present invention. Inflammatory diseases and conditions cover a wide range of indications. Many diseases or conditions which are seemingly unrelated to inflammation have inflammatory components that can be treated with the EL-Fs and/or devices according to the present invention. The skin diseases and conditions mentioned in the present invention all have inflammatory components, such as acne, psoriasis, atopic dermatitis, eczema. A non limiting selection of further inflammatory diseases and conditions that can be treated with EL-Fs and/or devices according to the invention is arthritis, inflammatory bowel disease, gingival inflammation, inflammation of the mucosa, inflammation of the nail bed, arteriosclerosis, and inflammation of the vascular system.

Preferred wavelengths for the treatment and/or prophylaxis of inflammation are in the range between 350 and 900 nm, particularly preferably between 380 and 900 nm, and very particularly preferably between 400 and 860 nm. Further preferred wavelengths for the treatment and/or prophylaxis of inflammation are 405, 420, and 850 nm.

Said EL-Fs and/or devices can be used for the treatment and/or prophylaxis of infections. Infections can be caused by bacteria and viruses. Light has several positive effects on infections. Light has, e.g., anti-inflammatory effects through the stimulation of the tissue as outlined elsewhere within the present invention.

Phototherapy with EL-Fs and/or devices according to the present invention is beneficial for the use to treat wounds. Wound healing is often associated with inflammation. Therefore the same wavelengths and ranges of wavelengths as outlined for the treatment and/or prophylaxis of inflammation can be applied. Treating wounds by phototherapy also prevents the formation of scares. Particularly preferred wavelengths for the treatment and/or prophylaxis of wounds and/or scares are in the range between 600 and 950 nm and very particularly preferably between 650 and 900 nm. Further preferred wavelengths for the treatment and/or prophylaxis of wounds and scares are 660, 720, and 880 nm.

Other infections that can efficiently be treated with EL-Fs and/or devices according to the present invention are caused by bacteria.

Further infections that can efficiently be treated with EL-Fs and/or devices according to the present invention are caused by viruses. A preferred embodiment of this invention is the use of the said EL-Fs and/or devices for the treatment and/or prophylaxis of viral infections particularly caused by cytomegalovirus (CMV), encephalo myocarditis virus (EMCV), poliovirus, influence virus, parainfluenza respiratory influenza virus, respiratory syncytial virus, Japanese encephalitis virus, Dengue virus, hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV) Epstein Barr Virus (EBV), human immunodeficiency virus type 1 (HIV-I), human immunodeficiency virus type 2 (HIV-2), varicella zoster virus, herpes simplex virus, in particular herpes simplex virus type 1 (HSV-I), herpes simplex virus type 2 (HSV-2), or human herpes virus 1, 2, 3, 4, 7, or 8, Kaposi's sarcoma-associated herpesvirus (KSHV), rotavirus, papilloma virus, and human papilloma virus (HPV), in particular HPV of the types: 1, 2, 3, 4, 5, 8, 9, 11, 12, 13, 14, 15, 16, 17, 18, 19-29, 31, 32, 34, 36-38, 46-50, 56, or 58.

In particular viral skin diseases and/or tumor disorders can be treated with EL-Fs and/or devices according to the present invention such as genital warts, benign tumors of the skin and/or mucosa caused by papilloma viruses, in particular verrucae plantares, verrucae vulgares, verrucae planae juveniles, epidermodysplasia verruciformis, Condylomata acuminate, Condylomata plana, bowenoid papulosis, papilloma on the larynx and oral mucosa, focal epithelial hyperplasia, herpes labialis, varicella and shingles.

In a particularly preferred embodiment of the present invention the EL-Fs and/or devices of the invention can be used for the treatment and/or prophylaxis of warts. Pulsed light therapy might be one way to treat warts with EL-Fs and/or devices according to the present invention.

EL-Fs and/or devices according to the present invention for the treatment and/or prophylaxis of neurological or psychological diseases and/or conditions is also subject of the present invention.

A preferred neurological disease according to the present invention is Morbus Parkinson (MB). When light reaches a certain level of intensity, it inhibits melatonin which in turn limits the production of dopamine. By limiting the melatonin is supposed to lead to a have better production and use of dopamine in the brain. Recent case studies of light therapy on MB patients involving bright light therapy have had positive results with marked improvement in bradykinesia and rigidity in most patients while being exposed for only ninety minutes.

Further preferred neurological and psychological diseases and/or conditions according to the present invention are mood and sleep related. Light is well known to be beneficial on the mood in many circumstances. Phototherapy can also be employed to treat depression, seasonal affective disorder (SAD), non seasonal depression, circadian rhythm sleep disorder (chronic circadian rhythm sleep disorder (CRSD), situational CRSD).

The US National Library of Medicine notes that some people experience a serious mood change when the seasons change. They may sleep too much, have little energy, and crave sweets and starchy foods. They may also feel depressed. Though symptoms can be severe, they usually clear up. The condition in the summer is often referred to as Reverse Seasonal Affective Disorder, and can also include heightened anxiety. It has been estimated that 1.5 to 9% of adults in the US experience SAD.

There are different treatments for classic (winter-based) seasonal affective disorder, including light therapy with bright lights, antidepressant medication, cognitive-behavioral therapy, ionized-air administration, and carefully timed supplementation of the hormone melatonin.

The wavelength for the treatment and/or prophylaxis of these neurological and psychological diseases and/or conditions that is to be emitted by said EL-Fs and/or devices is in the range between 350 and 600 nm. Preferably the wavelength is in the range between 400 and 550 nm, and particularly preferably between 440 and 500 nm. Two particular preferred wavelengths for this purpose are 460 and 480 nm.

The EL-Fs and/or devices according to the present invention may also be used for the treatment and/or prophylaxis of pain. Pain relief by phototherapy is well known. The following conditions produce pain that can be treated successfully with phototherapy: carpal tunnel syndrome, chronic wounds, epicondylitis, headache, migraine, plantar fasciitis, tendonditis and bursitis, neck pain, back pain, muscle pain, trigeminal neuralgia, and Whiplash-associated injuries.

Preferably, muscle pain is treated with EL-Fs and/or devices emitting red or infrared light.

Alopecia areata is a condition affecting humans, in which hair is lost from some or all areas of the body, usually from the scalp. Because it causes bald spots on the scalp, especially in the first stages, it is sometimes called spot baldness. In 1 to 2% of cases, the condition can spread to the entire scalp (alopecia totalis) or to the entire epidermis (alopecia universalis). Conditions resembling alopecia areata, and having a similar cause, occur also in other species.

Alopecia areata (autoimmune hair loss) can be treated by a EL-Fs and/or devices according to the present invention. The wavelength for the treatment and/or prophylaxis of alopecia areata that is to be emitted by the EL-Fs and/or devices according to the present invention is in the range between 240 and 500 nm. Preferably the wavelength is in the range between 290 and 400 nm, and particularly preferably between 300 and 330 nm. One particular preferred wavelength for this purpose is 311 nm.

Said EL-Fs and/or devices used for the disinfection and/or sterilization and/or preservation of beverages and nutrition is also subject of the present invention.

The use of light for the purpose of disinfection and/or sterilization and/or preservation is well known. The EL-Fs and/or devices according to the present invention can be used for this purpose. Hereby any kind of disinfection and/or sterilization and/or preservation is meant and includes without limitation the disinfection of wounds, nutrition, and solid and liquids objects, such cosmetic, medical devices, devices used for surgery and beverages.

Preference is given to EL-Fs and/or devices for the disinfection and/or sterilization and/or preservation of beverages, preferably water, and particularly preferably drinking water. Contaminated water causes many infections worldwide and leads often to severe diseases or death of the individuals.

Water filter systems of commercial providers take advantage of ion exchange technology. The filter, however, tend to microbial contamination, which, in turn results in water which is contaminated with microbes. One solution is to add silver salt which may be from a toxicological point of view problematic. The EL-Fs and/or devices of the present invention provide a solution to this problem. They can be used to be incorporated into the water filter system in order to provide a safe, efficient, and low cost way to provide water with a low degree of microbial contamination. The light source can irradiate both the water before or after filtering or the filter cartridge itself. Preferably the light source comprising the EL-Fs irradiates both the filter cartridge and the already filtered water.

The procedure of disinfection and/or sterilization and/or preservation of water as outlined above can basically be applied to any other liquid, in particular beverage analogously.

Therefore, the EL-Fs and/or devices according to the present invention can be used for the disinfection and/or preservation of beverages and nutrition for humans and animals.

Wavelengths for disinfection and/or sterilization and/or preservation according to the present invention are in the range between 200 nm and 600 nm, preferably between 250 nm and 500 nm, and very particularly preferably between 280 nm and 450 nm.

In another embodiment the present invention relates to the said EL-Fs and/or devices for the application in photodynamic therapy (PDT).

Wavelengths required for PDT according to the present invention are in the range between 300 and 700 nm, preferably between 400 and 700 nm, and very particularly preferably between 500 and 700 nm. Four further preferred wavelengths are 595, 600, 630, and 660 nm.

Any therapy known as PDT can be treated with EL-Fs and/or devices according to the present invention and devices comprising them. In particularly PDT as outlined within the present invention can be treated with EL-Fs and/or devices according to the present invention. The property of dyes with a polycyclic hydrocarbon type chemical structure to accumulate in greater amounts in tumor tissues than in normal tissues is well known. The dyes include acridines, xanthenes, psoralens, and porphyrins. The latter dyes, in particular, hematoporphyrin (Hp) and some of its chemical derivatives (e.g. Hp D, wherein Hp D is a mixture of Hp derivatives), have superior tumor-localizing properties, which are the basis of phototherapeutic treatment of tumors with red light irradiation at predetermined times after systemic administration of the drug.

Drug used for PDT are preferably selected from aminolevulinic acid/methyl aminolevulinate, efaproxiral porphyrin derivatives (porfimer sodium, talaporf in, temoporfin, verteporfin).

In a further embodiment the present invention relates to the said EL-Fs and/or devices for the treatment and/or prophylaxis of jaundice and crigler naijar, preferably jaundice.

Jaundice, which is also known as icterus, is a yellowish discoloration of the skin, the conjunctival membranes over the sclerae (whites of the eyes), and other mucous membranes. The discoloration is caused by hyperbilirubinemia (increased levels of bilirubin in the blood). This hyperbilirubinemia subsequently causes increased levels of bilirubin in the extracellular fluids. Jaundice is classified in three groups, pre-hepatic (hemolytic) jaundice, hepatic (hepatocellular) jaundice, and post-hepatic (obstructive) jaundice.

Pre-hepatic jaundice is caused by anything which causes an increased rate of hemolysis, i.e. breakdown of red blood cells. In tropical countries, malaria can cause jaundice in this manner. Certain genetic diseases, such as sickle cell anemia, spherocytosis and glucose 6-phosphate dehydrogenase deficiency can lead to increased red cell lysis and therefore hemolytic jaundice. Commonly, diseases of the kidney, such as hemolytic uremic syndrome, can also lead to coloration. Defects in bilirubin metabolism also present as jaundice. Jaundice usually comes with high fevers. Rat fever (leptospirosis) can also cause jaundice.

Hepatic jaundice causes include acute hepatitis, hepatotoxicity and alcoholic liver disease, whereby cell necrosis reduces the liver's ability to metabolise and excrete bilirubin leading to a buildup in the blood. Less common causes include primary biliary cirrhosis, Gilbert's syndrome (a genetic disorder of bilirubin metabolism which can result in mild jaundice, which is found in about 5% of the population), Crigler-Najjar syndrome, metastatic carcinoma and Niemann-Pick disease, type C. Jaundice seen in the newborn, known as neonatal jaundice, is common, occurring in almost every newborn as hepatic machinery for the conjugation and excretion of bilirubin does not fully mature until approximately two weeks of age.

Post-hepatic jaundice, also called obstructive jaundice, is caused by an interruption to the drainage of bile in the biliary system. The most common causes are gallstones in the common bile duct, and pancreatic cancer in the head of the pancreas. Also, a group of parasites known as "liver flukes" can live in the common bile duct, causing obstructive jaundice. Other causes include strictures of the common bile duct, biliary atresia, ductal carcinoma, pancreatitis and pancreatic pseudocysts. A rare cause of obstructive jaundice is Mirizzi's syndrome.

Jaundice, in particular neonatal jaundice, can lead to severe medical consequences if not or not appropriately treated. Increased concentrations of bilirubin can result in a brain-damaging condition known as kernicterus, leading to significant lifelong disability; there are concerns that this condition has been rising in recent years due to inadequate detection and treatment of neonatal hyperbilirubinemia. Early treatment often consists of exposing the infant to intensive phototherapy in an more or less isolated incubator. The therapy often represents an emotionally or psychologically difficult situation for both the infant and the parents. The EL-Fs and/or devices of the present invention can be employed in order to provide flexible and ambulatory devices such as blankets. Thus, the infant can be treated while laying in its parents' arms. Traditional therapies also easily lead to overheating of the infant, which can also be significantly reduced with the EL-Fs and/or devices of the present invention and devices comprising them.

Preferably the present invention relates to EL-Fs and/or devices used for the treatment of neonatal jaundice.

Jaundice of a subject can be treated by EL-Fs and/or devices according to the present invention. The wavelength for the treatment and/or prophylaxis of jaundice that is to be emitted by the EL-Fs and/or devices according to the present invention is in the range between 300 and 700 nm. Preferably the wavelength is in the range between 350 and 600 nm, and particularly preferably between 370 and 580 nm. Further preferred wavelengths are in the range between 400 and 550 nm. Particularly preferred wavelengths are in the range between 410 and 470 nm. Two particular preferred wavelengths for this purpose are 450 and 466 nm.

In another embodiment the present invention relates to the use of the EL-Fs for the preparation of a device for the treatment and or/prophylaxis of therapeutic diseases and/or cosmetic conditions. The therapeutic diseases and conditions are the same as the ones described elsewhere in the present invention.

Thus, the present invention also relates to a canvas comprising at least one fiber according to the present invention.

The present invention further relates to a device comprising at least one fiber according to the present invention or at least one canvas according to the present invention.

The said device is preferably a flat panel, curved panel, plaster, bandage, blanket, sleeping bag, sleeve, implantable probe, nasogastric tube, chest drain, pad, stent, patch, any kind of clothes, and devices covering at least one tooth in the mouth.

The present invention also relates to said device for use in medicine for phototherapy.

In particular, the present invention relates to said device for use for the treatment and/or prophylaxis of human or animal skin diseases preferably selected from psoriasis, eczema, dermatitis, atopic dermatitis, atopic eczema, edema, vitiligo, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, and radiodermatitis.

Furthermore, the present invention relates to said device for use for the treatment and/or prophylaxis of infections and inflammatory, neurological, and psychological diseases and/or conditions, jaundice and crigler naijar The present invention also relates to a method for cosmetical treatment of the skin by employing a device according to the present invention in order to irradiate human and animal skin, preferably human skin.

Preferably the method is used in order to reduce and/or prevent skin ageing, the formation of skin wrinkles, cellulite, acne, comedo, and skin redness The present invention also relates to the use of said devices for the preservation, sterilization and/or disinfection of water, drinking water, soft drinks, beverages, foodstuff, and nutrition.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The teaching as disclosed here can be abstracted and combined with other examples disclosed.

Other features of the invention will become apparent in the course of the following description of exemplary embodiments and drawings, which are given for illustration of the invention and are not intended to be limiting thereof.

WORKING EXAMPLES

Materials

Figure 1:
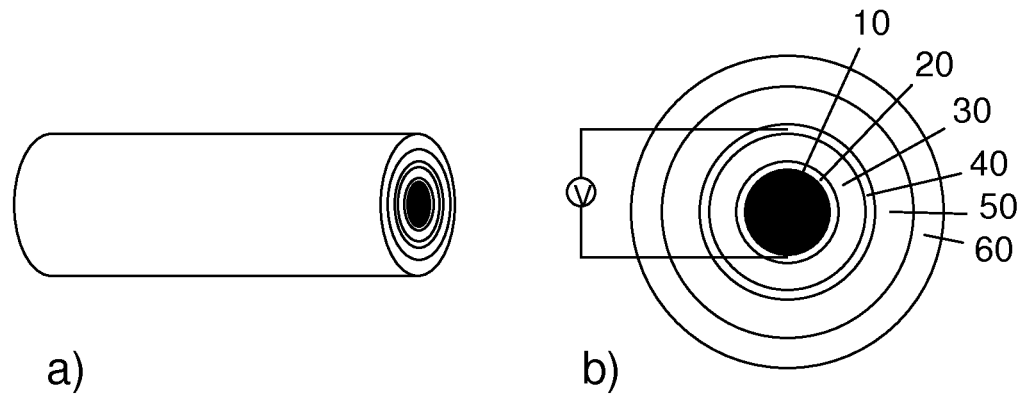
FIG. 1: Fiber with a fiber core 10 having an outer first electrode 20, a light emitting layer 30, a radiation transmissive second electrode 40 positioned over the organic light emitting layer 30. Eventually the OLEFC may also comprise an optional radiation transmissive moisture and/or air barrier layer 50 and/or an optional radiation transmissive encapsulating material 60.

The following materials are used in the present invention as examples.

Host (homo-)polymer P1 (WO 2007/085377A2):

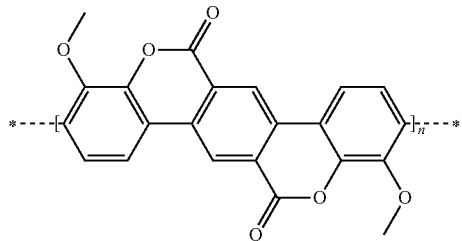

The detailed synthesis of P1 is described in Tetrahedron Letters 47 (2006) 8689-8692.

Quantum dot (QD1) is a core-shell type quantum-dot by Plasmachem GmbH, Berlin, Germany, having a CdSe spheric core capped with epitaxial ZnS shell. QD1 has a surface hydrophobic layer comprising mostly trioctylphosphine oxide. The photoluminescent quantum efficiency (PLQE) of QD1 is measured using Rhodamine 6G as reference and is found to be about 30%.

TM, as disclosed by Chen et al. (J. Materials Chemistry, 2009, 19, 8112-8118), is a triplet matrix material, having a wide band gap, e.g. HOMO of −6.47 eV and LUMO of −2.8 eV according to time dependent DFT method, as described above or below. Here TM will be used as electron transport material, or buffer layer between emissive layer (EML) and cathode.

TM:

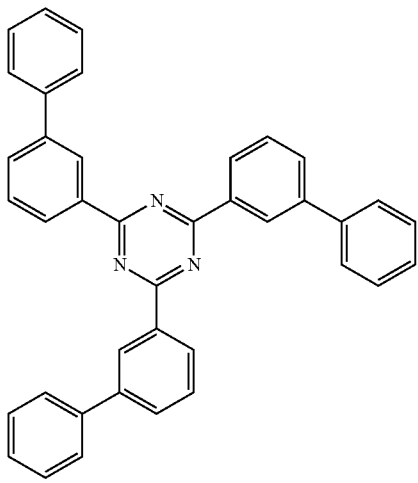 [SMILES: c1ccc(-c2cccc(-c3nc(-c4cccc(-c5ccccc5)c4)nc(-c4cccc(-c5ccccc5)c4)n3)c2)cc1]

Triplet green emitter TEG1:

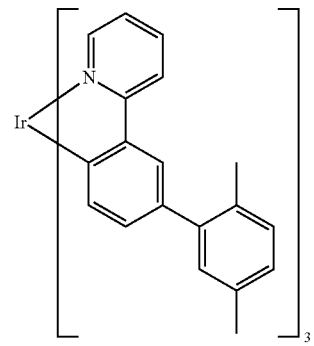

Triplet matrix material TMM1 (WO 2005/053055)

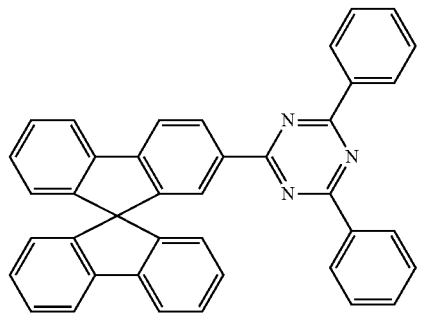 [SMILES: c1ccc(-c2nc(-c3ccccc3)nc(-c3ccc4c(c3)C3(c5ccccc5-c5ccccc53)c3ccccc3-4)n2)cc1]

Triplet matrix material TMM2 (WO 2009/124627)

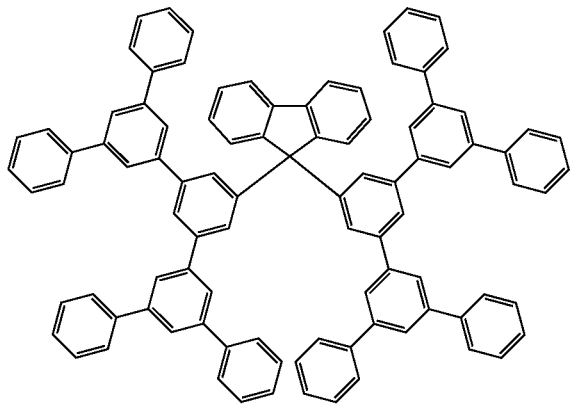 [SMILES: c1ccc(-c2cc(-c3ccccc3)cc(-c3cc(-c4cc(-c5ccccc5)cc(-c5ccccc5)c4)cc(C4(c5cc(-c6cc(-c7ccccc7)cc(-c7ccccc7)c6)cc(-c6cc(-c7ccccc7)cc(-c7ccccc7)c6)c5)c5ccccc5-c5ccccc54)c3)c2)cc1]

Non-conjugated polymeric triplet matrix P2 (see WO 2010/136111 for synthesis of P2):

Singlet blue emitter SEB1 (WO 2008/006449)

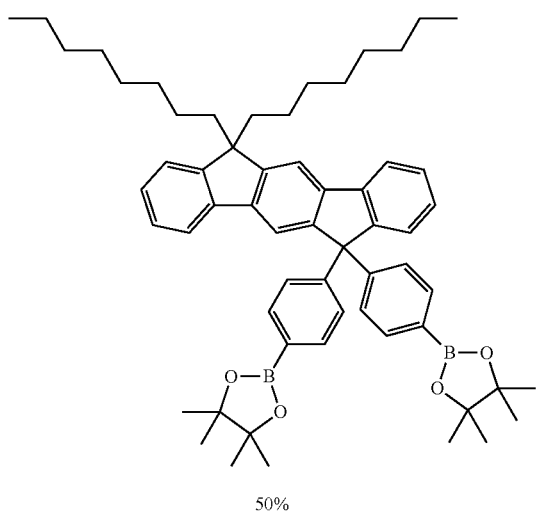

50%

+

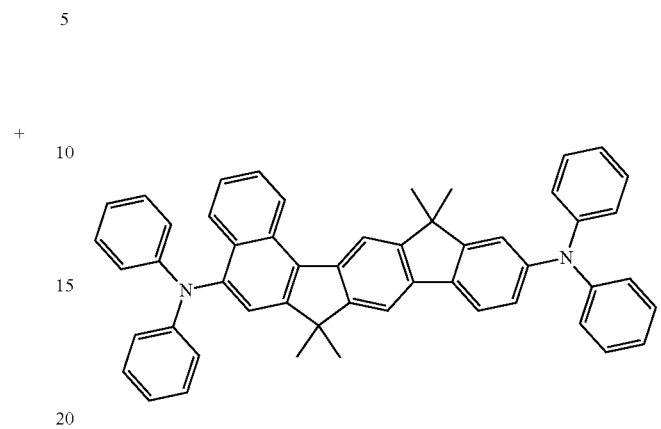

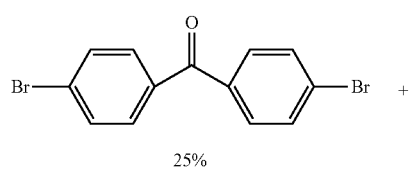

25%

+

SPB-090 is a blue polymer by Merck KGaA. HIL-012 is a hole transport and electron blocking material by Merck KGaA, and will be used as interlayer (IL).

Example 1

Fabrication of Light Emitting Fibers (LEFs)

Different light emitting fibers, both OLEDs and OLECs, are prepared. The device structures are listed in Table 1, wherein the layer thicknesses are shown in parentheses. In general, the thickness of emissive layer (EML) for fiber OLEDs is 80 nm and for fiber OLECs is 250 nm; and cathode for fiber OLED, except for LEF1, is LiF(1)/Al(100), and for fiber OLEC is Ag(20). LEF1 has 10 nm $WO_3$ as hole injection layer or charge generation layer, and TM as electron transport layer.

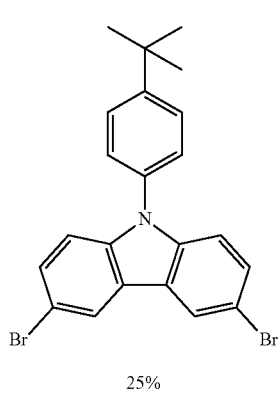

25%

Matrix for singlet singlet system SMB1 (WO 2007/065678)

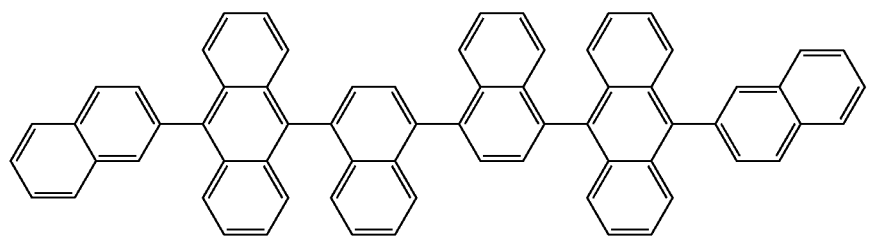 [SMILES: c1ccc2cc(-c3c4ccccc4c(-c4ccc(-c5ccc(-c6c7ccccc7c(-c7ccc8ccccc8c7)c7ccccc67)c6ccccc56)c5ccccc45)c4ccccc34)ccc2c1]

TABLE 1

Layer Structure of LEF1-10

Device Structure

| | Anode | Buffer Layer | Interlayer | EML | ETL | Cathode |
|---|---|---|---|---|---|---|
| LEF1 | Al(50)/Ni(5)//WO3(10) | — | — | EML(80) | TMM-127(25) | LiF(1)/Al(20) |
| LEF2 | Al(50)/Ni(5) | PEDOT(80) | HIL-012(20) | EML(250) | — | Ag(20) |
| LEF3 | Al(50)/Ni(5) | PEDOT(80) | HIL-012(20) | EML(80) | — | Ba(3)/Ag(15) |
| LEF4 | Al(50)/Ni(5) | PEDOT(80) | HIL-012(20) | EML(250) | — | Ag(20) |
| LEF5 | Al(50)/Ni(5) | PEDOT(80) | HIL-012(20) | EML(80) | — | Ba(3)/Ag(15) |
| LEF6 | Al(50)/Ni(5) | PEDOT(80) | HIL-012(20) | EML(250) | — | Ag(20) |
| LEF7 | Al(50)/Ni(5) | PEDOT(80) | HIL-012(20) | EML(80) | — | Ba(3)/Ag(15) |
| LEF8 | Al(50)/Ni(5) | PEDOT(80) | HIL-012(20) | EML(250) | — | Ag(20) |
| LEF9 | Al(50)/Ni(5) | PEDOT(80) | HIL-012(20) | EML(80) | — | Ba(3)/Ag(15) |
| LEF10 | Al(50)/Ni(5) | PEDOT(80) | HIL-012(20) | EML(250) | — | Ag(20) |

The composition of EML, solution for coating EML and the heat-treatment conditions for EML are listed in Table 2:

TABLE 2

Composition and solution for coating EML and heat treatment condition

| | Composition for EML [wt %] | Concentration [mg/ml] | Heating conditions EML | EML thickness [nm] |
|---|---|---|---|---|
| LEF1 | 80% P1:20% QD1 | 24 | 10 min @ 180° C. | 80 |
| LEF2 | 36% P1:36% PEO: 8% LiTrf:20% QD1 | 24 | 30 min @ 60° C. | 250 |
| LEF3 | 30% TMM1:30% TMM2: 20% TEG1:20% QD1 | 24 | 10 min @ 180° C. | 80 |
| LEF4 | 13.5% TMM1:13.5% TMM2: 9% TEG1:36% PEO: 8% LiTrf:20% QD1 | 24 | 30 min @ 60° C. | 250 |
| LEF5 | 60% P2:20% TEG1: 20% QD1 | 12.5 | 10 min @ 180° C. | 80 |
| LEF6 | 27% P2:9% TEG1: 36% PEO:8% LiTrf: 20% QD1 | 12.5 | 30 min @ 60° C. | 250 |
| LEF7 | 90% SMB1:5% SEB1: 5% QD1 | 16 | 30 min @ 120° C. | 80 |
| LEF8 | 40.5% SMB1:5% SEB1: 40.5% PEO:9% LiTrf: 5% QD1 | 16 | 30 min @ 60° C. | 250 |
| LEF9 | 80% SPB-090:20% QD1 | 12.5 | 10 min @ 180° C. | 80 |
| LEF10 | 36% SPB-090:36% EPO: 8% LiTrf:20% QD1 | 12.5 | 30 min @ 60° C. | 250 |

The fiber used in the present invention is a so called hard polymer-clad silica optical fiber (by CeramOptec Industries, Inc.), which has a silica core of 400 µm in diameter and 25 µm polyimide as jacket. Prior to the deposition of electrode, the fibers are cleaned successively by rubbing with a detergent, rinsing in de-ionized water, and cleaning by sonication in trichloroethylene, acetone and then isopropyl alcohol.

Figure 2:
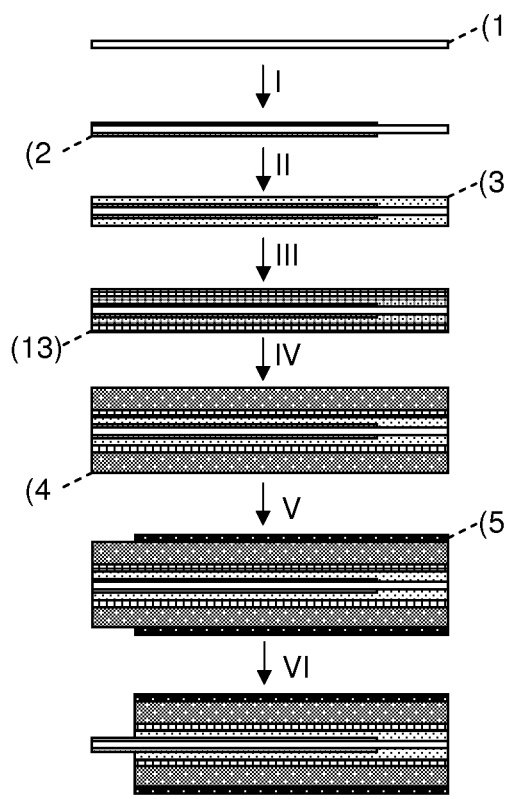
FIG. 2: One way to prepare a fiber comprising the following steps. Step I: deposition of anode 20 on fiber core 10; step II: deposition of buffer layer 31; step III: deposition of interlayer 32; step IV: deposition of emissive layer 33; step V: deposition of cathode 40; step VI: free anode
Figure 3:
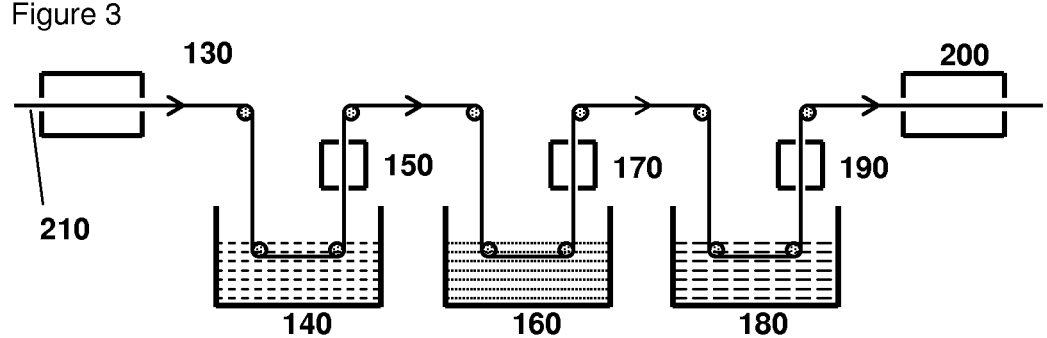
FIG. 3: Fiber production line by employing dip coating. 210—fiber core; 130—deposition chamber for the first electrode; 200—deposition chamber for the second electrode; 140—container containing solution of buffer material or HIM; 160—container containing a solution or a formulation of HTM or interlayer material; 180—container containing a solution or a formulation of an emissive composition; 150, 170, and 190 are dryers.
Figure 4:
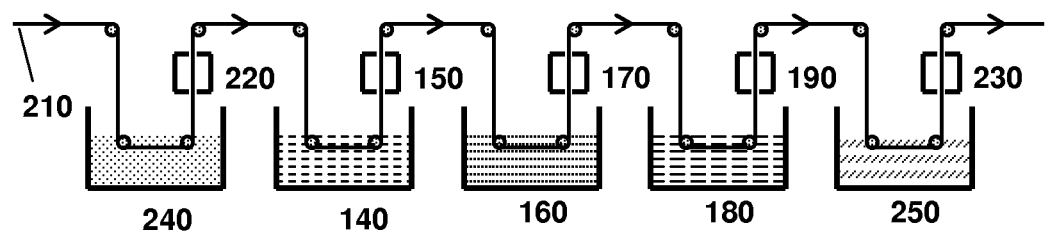
FIG. 4: Production method which is all solution based. 250—container containing an ink comprising a conductive material for the second electrode; 220 and 230 are dryers; 240—container comprising an ink comprising a conductive material for the first electrode.

The fabrication steps are schematically depicted in the FIG. 2.

Step I: Deposition of Anode

The anode (2), as in step V the cathode (5), is deposited conformally on the fiber core (1), which is a polymer-clad silica optical fiber by CeramOptec Industries, Inc., through a shadow mask using vacuum thermal evaporation at 10-7 Torr. The fibers are axially rotated at a speed of 60 rpm during the evaporation. The anode materials for different devices are listed in Table 1.

Step II: Deposition of Buffer Layer (3) (Except LEF1)

PEDOT (Baytron P AI 4083) is deposited as buffer layer or hole injection layer (HIL) with a thickness of 80 nm onto the fiber by dip-coating and then heated for 10 min. at 180° C.; the thickness can be controlled through the concentration and the pulling speed during the dip-coating. The fiber is then heated for 10 min. at 180° C. to remove the residual water.

Step III: Deposition of Interlayer (13) (Except LEF1)

Interlayer (13) is then coated by dip-coating from a toluene solution comprising interlayer polymer HIL-012 with a concentration of 0.1 to 0.5 wt % yielding a layer with a thickness of about 40 nm;

The thickness of the film on the fiber can be determined as follows. A flat glass substrate is coated by dip-coating in the same solution; the thickness of the film on glass substrate is then measured by Surface Profiler (Dektak3 ST). The concentration of the solution and pulling speeding are adjusted until the desired thickness is obtained. The same method is applied to interlayer and EML coating as described above and below.

Interlayer (13) is heated at 180° C. for 60 min. to remove residual solvent and in order to immobilize the polymer;

Step IV: Deposition of Emissive Layer (EML) (4)

Emissive layer (EML) (4) is then coated by dip-coating a chlorbenzene solution comprising emissive materials yielding a layer with a desired thickness. The solution and the EML thicknesses are listed in Table 2.

The thickness of the film on the fiber was determined as follows. A flat glass substrate was coated by dip-coating in the same solution; the thickness of the film on glass substrate was then measured by Surface Profiler (Dektak3 ST). The concentration of the solution and pulling speeding are so adjusted until the desired thickness is obtained. The same condition, concentration and pulling speed will be applied to coat the corresponding film on the fiber.

The device is heated to remove the residual solvent; the heat-treatment conditions are listed in Table 2.

Step V: Cathode (5) Deposition

Cathode, as listed in Table 2, is conformally deposited through a shadow mask by thermal vacuum evaporation onto the emissive layer with a desired thickness; both anode and cathode along the fiber is 4 cm in one segment. And they displace with each other so that having an overlapping area 3 cm, corresponding to the emissive area on the fiber.

Only for LEF1, before cathode deposition, 25 nm TMM-127 was conformally deposited through a shadow mask by thermal vacuum evaporation at 10-7 Torr onto the emissive layer.

Step VI: Free Anode

The Fiber is cut into segments of 5 cm in length. One end of the cutted fiber, where no cathode is deposited, is washed away at first with toluene and then with ethanol, to remove the polymer and PEDOT to free anode in order to contact.

Example 2

Measurements and Results

LEF1-10 are characterized in house, VIL characteristics, driving voltages, EL spectrum and color coordinates properties are recorded.

The performance of EL-Fs is summarized in the Table 3, wherein Uon stands for turn-on voltage, CIE for CIE 1931 color coordinates.

TABLE 3

|  | Uon [V] | CIE @ 6 V |
| --- | --- | --- |
| LEF1 | 2.7 | 0.67/0.33 |
| LEF2 | 2.9 | 0.67/0.34 |
| LEF3 | 2.8 | 0.68/0.33 |
| LEF4 | 2.9 | 0.67/0.32 |
| LEF5 | 2.7 | 0.67/0.33 |
| LEF6 | 3.1 | 0.66/0.31 |
| LEF7 | 2.9 | 0.67/0.33 |
| LEF8 | 3.3 | 0.65/0.32 |
| LEF9 | 2.6 | 0.67/0.33 |
| LEF10 | 2.8 | 0.67/0.32 |

Example 3

EL Devices with Nanorods

CdSe/Cd Score/shell nanorods (hereafter called as NR1) can be synthesized according to Carbone, L et al., in Nano Lett. 2007, 7, 2942-2950.

The following solutions are prepared:
Solution1: 30% TMM1:30% TMM2:20% TEG1:20% NR1 in toluene having a concentration of 24 mg/ml;
Solution2: 13.5% TMM1:13.5% TMM2:9% TEG1:36% PEO:8% LiTrf:20% NR1 in cyclohexanone having a concentration of 24 mg/ml;

The reference devices, Ref1 and Ref2, on flat substrate using soltuion1 and solution2 are prepared as follows:
1. Deposition of 80 nm PEDOT (Baytron P AI 4083) as hole injection layer (HIL) onto an ITO coated glass substrate by spin coating, then heat-treatment 180° C. for 10 minutes.
2. Deposition of 20 nm interlayer by spin coating from toluene solution of HIL-012 having a concentration of 0.5% wt/l in glovebox.
3. Heating interlayer layer at 180° C. for 1 h in glovebox.
4. Deposition of emissive layer (EML) from Solution1 or Solution2 using dip-coating;
5. Heating the device to remove the residual solvent;
6. Deposition a cathode (3 nmBa/100 nmAl for Ref1 and 150 nm Al for Ref2) over the EML by vacuum thermal evaporation;
7. Encapsulation Fiber devices, NRF1 and NRF2, are prepared using the same procedure as for LEF3 and LEF4, except that for NRF1 the solution1 is used, and for NRF2 Solution2 is used.

Electroluminescent spectrum is determined using an Ocean Optics USB2000 spectrometer at a driving voltage of 6 V. A sheet polarizer is used to measure the electroluminescence intensities parallel ($I_1$) and perpendicular ($I_2$) to the fiber. And the degree of linear polarization can be calculated by: $(I_1-I_2)/(I_1+I_2)$.

For Ref1 and Ref2, no EL spectrum can be recorded. This is mainly due to the film quality of the EML containing nanorods are very low. The EMLs are very rough. However, for NRF1 and NRF2, clear EL spectrum can be measured for both devices. The maximum polarisation ratios are about 0.41 for NRF1 and 0.25 for NRF2.

The invention claimed is:

1. An electroluminescent fiber comprising an emissive layer (EML) and at least one nanocrystal, which is either electrically neutral or ionic, wherein the fiber is an organic light emitting electrochemical cell (OLEC, LEC, LEEC) comprising at least one mobile ionic species in the EML, and wherein the nanocrystal is selected from mono-dispersive quantum dot or mono-dispersive nanorod.

2. The fiber according to claim 1, wherein the fiber comprises
    a) a fiber core, which is either flexible or rigid, having an outer first electrode;
    b) an EML comprising at least one emissive nanocrystal and/or at least one organic emissive compound, positioned over the outer surface of the said first electrode;
    c) a radiation transmissive second electrode positioned over the emissive layer.

3. The fiber according to claim 1, wherein the cross section of the fiber is circular, oval, or polygonal.

4. The fiber according to claim 1, wherein the fiber comprises at least one organic emissive compound selected from fluorescent emitter materials, phosphorescent emitter materials, and emissive organo metallic complexes.

5. The fiber according to claim 1, wherein the fiber comprises at least one host material and at least one emitter material, wherein the host material is selected from anthracenes, benzanthracenes, ketones, carbazoles, triarylamines, indeno-fluorenes, indenocarbazoles, indolocarbazoles, fluorenes, spirobifluorenes, phenanthrenes, dihydrophenanthrenes, thiophenes, triazines, imidazoles, isomers and derivatives thereof.

6. The fiber according to claim 1, wherein the fiber comprises at least one further functional material selected from hole transport materials (HTMs), hole injection materials (HIMs), electron transport materials (ETMs), and electron injection materials (EIMs), electron blocking materials (EBMs), and hole blocking materials (HBMs).

7. The fiber according to claim 1, wherein the nanocrystal is selected from the group consisting of Group II-VI, Group III-V, Group IV-VI and Group IV semiconductors.

8. The fiber according to claim 1, wherein the at least one emissive nanocrystal, which is electrically neutral, and at least one organic functional material selected from host materials, fluorescent emitters, phosphorescent emitters, HTMs, HIMs, ETMs, EIMs, hole blocking materials (HBMs), and electron blocking materials (EBMs), which is either electrically neutral or ionic are located in the EML of the fiber.

9. The fiber according to claim 1, wherein the device is a quantum-dot or nanorod light emitting diode (QD-LED or NR-LED).

10. The fiber according to claim 1 comprising at least one nanocrystal, at least one host material and at least one emitter, wherein the emission wavelength(s) of the emitter(s) is (are) shorter as compared to the emission wavelength(s) of the nanocrystal(s).

11. The fiber according to claim 1 comprising at least one nanocrystal and at least one further organic functional material selected from host materials and emissive materials, preferably emissive metal complexes in the EML, wherein the emission wavelength(s) of the emissive metal complexe(s) is (are) shorter as compared to the emission wavelength(s) of the nanocrystal(s).

12. Method for the preparation of the fiber according to claim 1 comprising the following steps: (1) cleaning the fiber core; (2) depositing of a first electrode; (3) depositing of an emissive layer comprising the nanocrystal(s); (4) depositing of a second electrode.

13. A canvas comprising at least one fiber according to claim 1.

14. A device comprising the fiber according to claim 1 and/or a canvas according to claim 13.

15. The device according to claim 14, wherein the device is a flat panel, curved panel, plaster, bandage, blanket, sleeping bag, sleeve, implantable probe, nasogastric tube, chest drain, pad, stent, patch, any kind of clothes, and devices covering at least one tooth in the mouth.

16. A method comprising irradiating an area of skin with the device according to claim 14 in medicine for phototherapy.

17. The method according to claim 16 wherein the phototherapy is treatment and/or prophylaxis of human or animal skin diseases preferably selected from psoriasis, eczema, dermatitis, atopic dermatitis, atopic eczema, edema, vitiligo, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, and radiodermatitis.

18. The method according to claim 16 wherein the phototherapy is treatment and/or prophylaxis of infections and inflammatory, neurological, and psychological diseases and/or conditions, jaundice and Crigler-Najjar syndrome.

19. A method for cosmetical treatment of the skin comprising utilizing the device according to claim 14 to irradiate human and animal skin.

20. The method according to claim 19 wherein the treatment is for the reduction and/or prevention of skin ageing, the formation of skin wrinkles, cellulite, acne, comedo, and skin redness.

21. A method for the preservation, sterilization and/or disinfection of water comprising irradiating drinking water, soft drinks, beverages, or foodstuff, with the device according to claim 14.

* * * * *